(12) United States Patent
Belson et al.

(10) Patent No.: US 8,517,923 B2
(45) Date of Patent: Aug. 27, 2013

(54) APPARATUS AND METHODS FOR FACILITATING TREATMENT OF TISSUE VIA IMPROVED DELIVERY OF ENERGY BASED AND NON-ENERGY BASED MODALITIES

(75) Inventors: Amir Belson, Cupertino, CA (US); Robert Matthew Ohline, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 568 days.

(21) Appl. No.: 10/850,360

(22) Filed: May 19, 2004

(65) Prior Publication Data

US 2005/0020901 A1    Jan. 27, 2005

Related U.S. Application Data

(63) Continuation-in-part of application No. 10/767,109, filed on Jan. 28, 2004, now abandoned, and a continuation-in-part of application No. 10/228,583, filed on Aug. 26, 2002, now Pat. No. 6,869,396, which is a continuation of application No. 09/790,204, filed on Feb. 20, 2001, now Pat. No. 6,468,203.

(60) Provisional application No. 60/194,140, filed on Apr. 3, 2000.

(51) Int. Cl.
*A61B 1/00* (2006.01)

(52) U.S. Cl.
USPC ............ 600/146; 600/114; 600/139; 600/142

(58) Field of Classification Search
USPC .............. 600/114–118, 146–152; 348/65–74
See application file for complete search history.

(56) References Cited

U.S. PATENT DOCUMENTS 616,672 A    12/1898  Kelling
2,510,198 A   6/1950  Tesmer
(Continued)

FOREIGN PATENT DOCUMENTS

DE    2823025    12/1979
DE    3707787     9/1988
(Continued)

OTHER PUBLICATIONS

Belson et al; U.S. Appl. No. 11/796,220 entitled "Steerable segmented endoscope and method of insertion," filed Apr. 27, 2007.

(Continued)

*Primary Examiner* — Matthew J Kasztejna

(57) ABSTRACT

Methods and apparatus for accessing and treating regions of the body are disclosed herein. Using an endoscopic device having an automatically controllable proximal portion and a selectively steerable distal portion, the device generally may be advanced into the body through an opening. The distal portion is selectively steered to assume a selected curve along a desired path within the body which avoids contact with tissue while the proximal portion is automatically controlled to assume the selected curve of the distal portion. The endoscopic device can then be used for accessing various regions of the body which are typically difficult to access and treat through conventional surgical techniques because the device is unconstrained by "straight-line" requirements. Various applications can include accessing regions of the brain, thoracic cavity, including regions within the heart, peritoneal cavity, etc., which are difficult to reach using conventional surgical procedures.

14 Claims, 19 Drawing Sheets

(56) References Cited

U.S. PATENT DOCUMENTS

| | | |
|---|---|---|
| 2,533,494 A | 12/1950 | Mitchell, Jr. |
| 2,767,705 A | 10/1956 | Moore |
| 3,060,972 A | 10/1962 | Sheldon |
| 3,071,161 A | 1/1963 | Ulrich |
| 3,096,962 A | 7/1963 | Meijs |
| 3,162,214 A | 12/1964 | Bazinet, Jr. |
| 3,168,274 A | 2/1965 | Street |
| 3,190,286 A | 6/1965 | Stokes |
| 3,266,059 A | 8/1966 | Stelle |
| 3,430,662 A | 3/1969 | Guarnaschelli |
| 3,497,083 A | 2/1970 | Anderson |
| 3,546,961 A | 12/1970 | Marton |
| 3,610,231 A | 10/1971 | Takahashi |
| 3,625,084 A | 12/1971 | Low |
| 3,643,653 A | 2/1972 | Takahashi et al. |
| 3,739,770 A | 6/1973 | Mori |
| 3,773,034 A | 11/1973 | Burns et al. |
| 3,780,740 A | 12/1973 | Rhea |
| 3,858,578 A | 1/1975 | Milo |
| 3,871,358 A | 3/1975 | Fukuda et al. |
| 3,897,775 A | 8/1975 | Furihata |
| 3,913,565 A | 10/1975 | Kawahara |
| 3,946,727 A | 3/1976 | Okada |
| 3,990,434 A | 11/1976 | Free |
| 4,054,128 A | 10/1977 | Seufert |
| 4,176,662 A | 12/1979 | Frazer |
| 4,233,981 A | 11/1980 | Schomacher |
| 4,236,509 A | 12/1980 | Takahashi |
| 4,240,435 A | 12/1980 | Yazawa et al. |
| 4,273,111 A | 6/1981 | Tsukaya |
| 4,327,711 A | 5/1982 | Takagi |
| 4,366,810 A | 1/1983 | Slanetz, Jr. |
| 4,393,728 A | 7/1983 | Larson |
| 4,432,349 A | 2/1984 | Oshiro |
| 4,483,326 A | 11/1984 | Yamaka et al. |
| 4,489,826 A | 12/1984 | Dubson |
| 4,494,417 A | 1/1985 | Larson |
| 4,499,895 A | 2/1985 | Takayama |
| 4,503,842 A | 3/1985 | Takayama |
| 4,543,090 A | 9/1985 | McCoy |
| 4,551,061 A | 11/1985 | Olenick |
| 4,559,928 A | 12/1985 | Takayama |
| 4,566,843 A | 1/1986 | Iwatsuka |
| 4,577,621 A | 3/1986 | Patel |
| 4,592,341 A | 6/1986 | Omagari et al. |
| 4,601,283 A | 7/1986 | Chikama |
| 4,601,713 A | 7/1986 | Fuqua |
| 4,621,618 A | 11/1986 | Omagari |
| 4,624,243 A | 11/1986 | Lowery et al. |
| 4,630,649 A | 12/1986 | Oku |
| 4,643,184 A | 2/1987 | Mobin-Uddin |
| 4,646,722 A | 3/1987 | Silverstein et al. |
| 4,648,733 A | 3/1987 | Merkt |
| 4,651,718 A | 3/1987 | Collins et al. |
| 4,655,257 A | 4/1987 | Iwashita |
| 4,683,773 A | 8/1987 | Diamond |
| 4,686,963 A | 8/1987 | Cohen et al. |
| 4,712,969 A | 12/1987 | Kimura |
| 4,726,355 A | 2/1988 | Okada |
| 4,753,222 A | 6/1988 | Morishita |
| 4,753,223 A | 6/1988 | Bremer |
| 4,754,909 A | 7/1988 | Barker et al. |
| 4,784,117 A | 11/1988 | Miyazaki |
| 4,787,369 A | 11/1988 | Allred, III |
| 4,788,967 A | 12/1988 | Ueda |
| 4,793,326 A | 12/1988 | Shishido |
| 4,796,607 A | 1/1989 | Allred, III |
| 4,799,474 A | 1/1989 | Ueda |
| 4,800,890 A | 1/1989 | Cramer |
| 4,807,593 A | 2/1989 | Ito |
| 4,815,450 A | 3/1989 | Patel |
| 4,832,473 A | 5/1989 | Ueda |
| 4,834,068 A | 5/1989 | Gottesman |
| 4,873,965 A | 10/1989 | Danieli |
| 4,873,990 A | 10/1989 | Holmes et al. |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A | 2/1990 | Takayama et al. |
| 4,904,048 A | 2/1990 | Sogawa et al. |
| 4,917,114 A | 4/1990 | Green et al. |
| 4,919,112 A | 4/1990 | Siegmund |
| 4,930,494 A | 6/1990 | Takehana et al. |
| 4,949,927 A | 8/1990 | Madocks et al. |
| 4,957,486 A | 9/1990 | Davis |
| 4,969,709 A | 11/1990 | Sogawa et al. |
| 4,971,035 A | 11/1990 | Ito |
| 4,977,886 A | 12/1990 | Takehana et al. |
| 4,977,887 A | 12/1990 | Gouda |
| 4,987,314 A | 1/1991 | Gotanda et al. |
| 5,005,558 A | 4/1991 | Aomori |
| 5,005,559 A | 4/1991 | Blanco et al. |
| 5,014,709 A | 5/1991 | Bjelkhagen et al. |
| 5,018,509 A | 5/1991 | Suzuki et al. |
| 5,025,778 A | 6/1991 | Silverstein et al. |
| 5,060,632 A | 10/1991 | Hibino et al. |
| 5,092,901 A | 3/1992 | Hunter et al. |
| 5,125,395 A | 6/1992 | Adair |
| 5,127,393 A | 7/1992 | McFarlin et al. |
| 5,159,446 A | 10/1992 | Hibino et al. |
| 5,166,787 A | 11/1992 | Irion |
| 5,174,276 A | 12/1992 | Crockard |
| 5,174,277 A | 12/1992 | Matsumaru |
| 5,188,111 A | 2/1993 | Yates et al. |
| 5,207,695 A | 5/1993 | Trout, III |
| 5,217,001 A | 6/1993 | Nakao et al. |
| 5,220,911 A | 6/1993 | Tamura |
| 5,228,429 A | 7/1993 | Hatano |
| 5,234,448 A | 8/1993 | Wholey et al. |
| 5,243,967 A | 9/1993 | Hibino |
| 5,250,058 A | 10/1993 | Miller et al. |
| 5,251,611 A | 10/1993 | Zehel et al. |
| 5,253,647 A | 10/1993 | Takahashi |
| 5,254,809 A | 10/1993 | Martin |
| 5,257,617 A | 11/1993 | Takahashi |
| 5,259,364 A | 11/1993 | Bob et al. |
| 5,269,289 A | 12/1993 | Takehana et al. |
| 5,271,381 A | 12/1993 | Ailinger et al. |
| 5,271,382 A | 12/1993 | Chikama |
| 5,279,610 A | 1/1994 | Park et al. |
| 5,297,443 A | 3/1994 | Wentz |
| 5,325,845 A | 7/1994 | Adair |
| 5,337,732 A | 8/1994 | Grundfest et al. |
| 5,337,733 A | 8/1994 | Bauerfeind |
| 5,343,874 A | 9/1994 | Picha |
| 5,347,987 A * | 9/1994 | Feldstein et al. ............ 600/109 |
| 5,348,259 A | 9/1994 | Blanco et al. |
| 5,370,108 A | 12/1994 | Miura et al. |
| 5,383,467 A | 1/1995 | Auer et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,400,769 A | 3/1995 | Tanii et al. |
| 5,402,768 A | 4/1995 | Adair |
| 5,411,508 A | 5/1995 | Bessler et al. |
| 5,413,108 A | 5/1995 | Alfano |
| 5,421,337 A | 6/1995 | Richards-Kortum et al. |
| 5,425,738 A | 6/1995 | Gustafson et al. |
| 5,429,118 A | 7/1995 | Cole et al. |
| 5,439,000 A | 8/1995 | Gunderson et al. |
| 5,451,221 A | 9/1995 | Cho et al. |
| 5,456,714 A | 10/1995 | Owen |
| 5,460,166 A | 10/1995 | Yabe et al. |
| 5,460,168 A | 10/1995 | Masubuchi et al. |
| 5,469,840 A | 11/1995 | Tanii et al. |
| 5,482,029 A | 1/1996 | Sekiguchi et al. |
| 5,487,385 A * | 1/1996 | Avitall ............ 600/374 |
| 5,487,757 A | 1/1996 | Truckai et al. |
| 5,489,256 A | 2/1996 | Adair |
| 5,507,287 A | 4/1996 | Palcic et al. |
| 5,507,717 A | 4/1996 | Kura et al. |
| 5,531,664 A | 7/1996 | Adachi et al. |
| 5,551,945 A | 9/1996 | Yabe et al. |

| Patent | Kind | Date | Inventor | Class |
|---|---|---|---|---|
| 5,558,619 | A | 9/1996 | Kami et al. | |
| 5,558,665 | A | 9/1996 | Kieturakis | |
| 5,577,992 | A | 11/1996 | Chiba et al. | |
| 5,586,968 | A | 12/1996 | Grundl et al. | |
| 5,590,660 | A | 1/1997 | MacAulay et al. | |
| 5,601,087 | A | 2/1997 | Gunderson et al. | |
| 5,602,449 | A | 2/1997 | Krause | |
| 5,620,408 | A | 4/1997 | Vennes et al. | |
| 5,624,380 | A | 4/1997 | Takayama et al. | |
| 5,624,381 | A | 4/1997 | Kieturakis | |
| 5,626,553 | A | 5/1997 | Frassica et al. | |
| 5,645,064 | A * | 7/1997 | Littmann et al. | 600/374 |
| 5,645,520 | A | 7/1997 | Nakamura et al. | |
| 5,647,368 | A | 7/1997 | Zeng et al. | |
| 5,647,840 | A * | 7/1997 | D'Amelio et al. | 600/169 |
| 5,651,769 | A | 7/1997 | Waxman et al. | |
| 5,653,690 | A | 8/1997 | Booth et al. | |
| 5,658,238 | A | 8/1997 | Suzuki et al. | |
| 5,662,585 | A | 9/1997 | Willis et al. | |
| 5,662,587 | A | 9/1997 | Grundfest et al. | |
| 5,665,050 | A | 9/1997 | Benecke | |
| 5,667,476 | A | 9/1997 | Frassica et al. | |
| 5,679,216 | A | 10/1997 | Takayama et al. | |
| 5,681,260 | A * | 10/1997 | Ueda et al. | 600/114 |
| 5,728,044 | A | 3/1998 | Shan | |
| 5,733,245 | A | 3/1998 | Kawano | |
| 5,749,828 | A | 5/1998 | Solomon et al. | |
| 5,752,912 | A | 5/1998 | Takahashi et al. | |
| 5,759,151 | A | 6/1998 | Sturges | |
| 5,762,613 | A | 6/1998 | Sutton et al. | |
| 5,765,561 | A | 6/1998 | Chen et al. | |
| 5,769,792 | A | 6/1998 | Palcic et al. | |
| 5,772,597 | A | 6/1998 | Goldberger et al. | |
| 5,773,835 | A | 6/1998 | Sinofsky | |
| 5,779,624 | A | 7/1998 | Chang | |
| 5,807,241 | A | 9/1998 | Heimberger | |
| 5,810,715 | A | 9/1998 | Moriyama | |
| 5,810,716 | A | 9/1998 | Mukherjee | |
| 5,810,717 | A | 9/1998 | Maeda | |
| 5,810,776 | A | 9/1998 | Bacich et al. | |
| 5,813,976 | A | 9/1998 | Filipi et al. | |
| 5,827,190 | A | 10/1998 | Palcic et al. | |
| 5,842,973 | A | 12/1998 | Bullard | |
| 5,848,972 | A * | 12/1998 | Triedman et al. | 600/508 |
| 5,860,581 | A | 1/1999 | Robertson et al. | |
| 5,860,914 | A | 1/1999 | Chiba et al. | |
| 5,876,329 | A | 3/1999 | Harhen | |
| 5,876,373 | A | 3/1999 | Giba et al. | |
| 5,885,208 | A | 3/1999 | Moriyama | |
| 5,893,369 | A | 4/1999 | LeMole | |
| 5,897,417 | A | 4/1999 | Grey | |
| 5,897,488 | A | 4/1999 | Ueda | |
| 5,902,254 | A | 5/1999 | Magram | |
| 5,906,591 | A | 5/1999 | Dario et al. | |
| 5,908,381 | A | 6/1999 | Aznoian et al. | |
| 5,916,147 | A | 6/1999 | Boury | |
| 5,921,915 | A | 7/1999 | Aznoian et al. | |
| 5,928,136 | A | 7/1999 | Barry | |
| 5,941,815 | A | 8/1999 | Chang | |
| 5,941,908 | A | 8/1999 | Goldsteen et al. | |
| 5,957,833 | A | 9/1999 | Shan | |
| 5,971,767 | A * | 10/1999 | Kaufman et al. | 434/267 |
| 5,976,074 | A | 11/1999 | Moriyama | |
| 5,989,182 | A | 11/1999 | Hori et al. | |
| 5,989,230 | A | 11/1999 | Frassica | |
| 5,993,381 | A | 11/1999 | Ito | |
| 5,993,447 | A | 11/1999 | Blewett et al. | |
| 5,996,346 | A | 12/1999 | Maynard | |
| 6,016,440 | A | 1/2000 | Simon et al. | |
| 6,033,359 | A | 3/2000 | Doi | |
| 6,036,636 | A | 3/2000 | Motoki et al. | |
| 6,042,155 | A | 3/2000 | Lockwood | |
| 6,048,307 | A | 4/2000 | Grundl et al. | |
| 6,063,022 | A | 5/2000 | Ben-Haim | |
| 6,066,102 | A | 5/2000 | Townsend et al. | |
| 6,066,132 | A | 5/2000 | Chen et al. | |
| 6,068,629 | A | 5/2000 | Haissaguerre et al. | |
| 6,068,638 | A | 5/2000 | Makower | |
| 6,096,289 | A | 8/2000 | Goldenberg | |
| 6,099,464 | A | 8/2000 | Shimizu et al. | |
| 6,099,465 | A | 8/2000 | Inoue | |
| 6,099,485 | A | 8/2000 | Patterson | |
| 6,106,510 | A | 8/2000 | Lunn et al. | |
| 6,119,913 | A | 9/2000 | Adams et al. | |
| 6,129,667 | A | 10/2000 | Dumoulin et al. | |
| 6,129,683 | A | 10/2000 | Sutton et al. | |
| 6,141,577 | A | 10/2000 | Roland | |
| 6,149,581 | A | 11/2000 | Klingenstein | |
| 6,162,171 | A | 12/2000 | Ng et al. | |
| 6,174,280 | B1 | 1/2001 | Oneda | |
| 6,174,291 | B1 | 1/2001 | McMahon et al. | |
| 6,178,346 | B1 * | 1/2001 | Amundson et al. | 600/473 |
| 6,179,776 | B1 | 1/2001 | Adams | |
| 6,185,448 | B1 | 2/2001 | Borovsky | |
| 6,201,989 | B1 | 3/2001 | Whitehead | |
| 6,203,493 | B1 | 3/2001 | Ben-Haim | |
| 6,203,494 | B1 | 3/2001 | Moriyama | |
| 6,210,337 | B1 | 4/2001 | Dunham et al. | |
| 6,221,006 | B1 | 4/2001 | Dubrul et al. | |
| 6,241,657 | B1 * | 6/2001 | Chen et al. | 600/117 |
| 6,249,076 | B1 | 6/2001 | Madden et al. | |
| 6,270,453 | B1 | 8/2001 | Sakai | |
| 6,306,081 | B1 | 10/2001 | Ishikawa et al. | |
| 6,309,346 | B1 | 10/2001 | Farhadi | |
| 6,315,714 | B1 | 11/2001 | Akiba | |
| 6,319,197 | B1 | 11/2001 | Tsuji et al. | |
| 6,327,492 | B1 | 12/2001 | Lemelson | |
| 6,332,089 | B1 | 12/2001 | Acker | |
| 6,348,058 | B1 | 2/2002 | Melkent | |
| 6,352,503 | B1 | 3/2002 | Matsui et al. | |
| 6,366,799 | B1 | 4/2002 | Acker | |
| 6,402,687 | B1 | 6/2002 | Ouchi | |
| 6,408,889 | B1 | 6/2002 | Komachi | |
| 6,428,203 | B1 | 8/2002 | Danley | |
| 6,443,888 | B1 | 9/2002 | Ogura et al. | |
| 6,453,190 | B1 | 9/2002 | Acker | |
| 6,459,481 | B1 | 10/2002 | Schaack | |
| 6,468,203 | B2 | 10/2002 | Belson | |
| 6,482,149 | B1 | 11/2002 | Torii | |
| 6,485,413 | B1 | 11/2002 | Boppart | |
| 6,490,467 | B1 | 12/2002 | Bucholz et al. | |
| 6,511,417 | B1 | 1/2003 | Taniguchi et al. | |
| 6,511,418 | B2 | 1/2003 | Shahidi | |
| 6,517,477 | B1 | 2/2003 | Wendlandt | |
| 6,527,706 | B2 | 3/2003 | Ide | |
| 6,537,211 | B1 | 3/2003 | Wang et al. | |
| 6,544,215 | B1 | 4/2003 | Bencini et al. | |
| 6,554,793 | B1 | 4/2003 | Pauker et al. | |
| 6,569,173 | B1 | 5/2003 | Blatter et al. | |
| 6,616,600 | B2 | 9/2003 | Pauker | |
| 6,638,213 | B2 | 10/2003 | Ogura et al. | |
| 6,641,528 | B2 | 11/2003 | Torii | |
| 6,656,110 | B1 | 12/2003 | Irion et al. | |
| 6,699,183 | B1 | 3/2004 | Wimmer | |
| 6,761,685 | B2 | 7/2004 | Adams et al. | |
| 6,783,491 | B2 | 8/2004 | Saadat et al. | |
| 6,790,173 | B2 | 9/2004 | Saadat et al. | |
| 6,800,056 | B2 | 10/2004 | Tartaglia et al. | |
| 6,808,499 | B1 | 10/2004 | Churchill et al. | |
| 6,808,520 | B1 | 10/2004 | Fourkas et al. | |
| 6,817,973 | B2 | 11/2004 | Merril et al. | |
| 6,837,846 | B2 | 1/2005 | Jaffe | |
| 6,837,847 | B2 | 1/2005 | Ewers et al. | |
| 6,837,849 | B2 | 1/2005 | Ogura et al. | |
| 6,843,793 | B2 | 1/2005 | Brock et al. | |
| 6,850,794 | B2 | 2/2005 | Shahidi | |
| 6,858,005 | B2 | 2/2005 | Ohline et al. | |
| 6,869,396 | B2 | 3/2005 | Belson | |
| 6,875,170 | B2 | 4/2005 | Francois et al. | |
| 6,890,297 | B2 | 5/2005 | Belson | |
| 6,902,528 | B1 | 6/2005 | Garibaldi et al. | |
| 6,942,613 | B2 | 9/2005 | Ewers et al. | |
| 6,960,161 | B2 | 11/2005 | Amiling et al. | |
| 6,960,162 | B2 | 11/2005 | Saadat et al. | |
| 6,960,163 | B2 | 11/2005 | Ewers et al. | |
| 6,974,411 | B2 | 12/2005 | Belson | |
| 6,984,203 | B2 | 1/2006 | Tartaglia et al. | |
| 7,018,331 | B2 | 3/2006 | Chang et al. | |

| | | | |
|---|---|---|---|
| 7,087,013 B2 | 8/2006 | Belson et al. | |
| 7,371,210 B2* | 5/2008 | Brock et al. ............... | 600/114 |
| 7,447,534 B1* | 11/2008 | Kingsley et al. ............ | 600/372 |
| 2002/0016607 A1 | 2/2002 | Bonadio et al. | |
| 2002/0062062 A1 | 5/2002 | Belson et al. | |
| 2002/0087049 A1* | 7/2002 | Brock et al. ............... | 600/114 |
| 2002/0120254 A1 | 8/2002 | Julian | |
| 2002/0147385 A1 | 10/2002 | Butler et al. | |
| 2002/0151767 A1 | 10/2002 | Sonnenschein | |
| 2002/0169361 A1 | 11/2002 | Taniguchi | |
| 2002/0193662 A1 | 12/2002 | Belson | |
| 2003/0083550 A1 | 5/2003 | Miyagi | |
| 2003/0086498 A1 | 5/2003 | Lee et al. | |
| 2003/0130598 A1 | 7/2003 | Manning et al. | |
| 2003/0167007 A1 | 9/2003 | Belson | |
| 2003/0182091 A1 | 9/2003 | Kukuk | |
| 2003/0195387 A1 | 10/2003 | Kortenbach et al. | |
| 2003/0233056 A1 | 12/2003 | Saadat et al. | |
| 2003/0236455 A1* | 12/2003 | Swanson et al. ............. | 600/374 |
| 2003/0236505 A1 | 12/2003 | Bonadio et al. | |
| 2003/0236549 A1 | 12/2003 | Bonadio et al. | |
| 2004/0000403 A1 | 1/2004 | Eoff et al. | |
| 2004/0019254 A1 | 1/2004 | Belson | |
| 2004/0044270 A1 | 3/2004 | Barry | |
| 2004/0049251 A1 | 3/2004 | Knowlton | |
| 2004/0097788 A1 | 5/2004 | Mourlas et al. | |
| 2004/0106852 A1 | 6/2004 | Windheuser et al. | |
| 2004/0176683 A1 | 9/2004 | Whitin et al. | |
| 2004/0186350 A1 | 9/2004 | Brenneman et al. | |
| 2004/0193008 A1 | 9/2004 | Jaffe et al. | |
| 2004/0193009 A1 | 9/2004 | Jaffe et al. | |
| 2004/0210109 A1 | 10/2004 | Jaffe et al. | |
| 2004/0220450 A1 | 11/2004 | Jaffe et al. | |
| 2005/0020901 A1 | 1/2005 | Belson et al. | |
| 2005/0085693 A1 | 4/2005 | Belson et al. | |
| 2005/0124855 A1 | 6/2005 | Jaffe et al. | |
| 2005/0137454 A1 | 6/2005 | Saadat et al. | |
| 2005/0137455 A1 | 6/2005 | Ewers et al. | |
| 2005/0137456 A1 | 6/2005 | Saadat et al. | |
| 2005/0154258 A1 | 7/2005 | Tartaglia et al. | |
| 2005/0154261 A1 | 7/2005 | Ohline et al. | |
| 2005/0165276 A1 | 7/2005 | Belson | |
| 2005/0168571 A1 | 8/2005 | Lia et al. | |
| 2005/0203339 A1 | 9/2005 | Butler et al. | |
| 2005/0209506 A1 | 9/2005 | Butler et al. | |
| 2005/0209509 A1 | 9/2005 | Belson | |
| 2005/0222497 A1 | 10/2005 | Belson | |
| 2005/0222498 A1 | 10/2005 | Belson | |
| 2005/0250990 A1 | 11/2005 | Le et al. | |
| 2006/0009678 A1 | 1/2006 | Jaffe et al. | |
| 2006/0052664 A1 | 3/2006 | Julian et al. | |
| 2006/0100642 A1 | 5/2006 | Yang et al. | |
| 2006/0235457 A1 | 10/2006 | Belson | |
| 2006/0235458 A1 | 10/2006 | Belson | |
| 2006/0258912 A1 | 11/2006 | Belson et al. | |
| 2007/0043259 A1 | 2/2007 | Jaffe et al. | |
| 2007/0093858 A1 | 4/2007 | Gambale et al. | |
| 2007/0135803 A1 | 6/2007 | Belson | |
| 2007/0161291 A1 | 7/2007 | Swinehart et al. | |
| 2007/0161857 A1 | 7/2007 | Durant et al. | |
| 2007/0249901 A1 | 10/2007 | Ohline et al. | |
| 2007/0270650 A1 | 11/2007 | Eno et al. | |

FOREIGN PATENT DOCUMENTS

| | | |
|---|---|---|
| DE | 19626433 A1 | 1/1998 |
| DE | 19729499 A1 | 1/1999 |
| EP | 0382974 A1 | 8/1990 |
| EP | 0497781 B1 | 1/1994 |
| EP | 0993804 A1 | 4/2000 |
| FR | 2732225 A1 | 10/1996 |
| GB | 2347685 A | 9/2000 |
| IE | 2000/0225 | 3/2000 |
| IE | 2000/0559 | 7/2000 |
| IE | 2002/0170 | 3/2002 |
| JP | 47-12705 | 5/1972 |
| JP | 63136014 | 6/1988 |
| JP | 63272322 | 11/1988 |
| JP | 1152413 | 6/1989 |
| JP | 1229220 | 9/1989 |
| JP | 01-262372 | 10/1989 |
| JP | 2246986 | 10/1990 |
| JP | 2296209 | 12/1990 |
| JP | 3136630 | 6/1991 |
| JP | 4054970 | 2/1992 |
| JP | 5011196 | 1/1993 |
| JP | 5111458 | 5/1993 |
| JP | 5305073 | 11/1993 |
| JP | 06-007287 | 1/1994 |
| JP | 07-116104 | 5/1995 |
| JP | 08-322786 | 12/1996 |
| JP | 09-028662 | 2/1997 |
| JP | 10337274 | 12/1998 |
| JP | 11042258 | 2/1999 |
| JP | 2001-046318 | 2/2001 |
| JP | 3322356 | 9/2002 |
| SU | 871786 | 10/1981 |
| SU | 1256955 | 9/1986 |
| SU | 1301701 | 4/1987 |
| WO | WO 93/17751 A1 | 9/1993 |
| WO | WO 94/19051 A1 | 9/1994 |
| WO | WO 95/04556 A2 | 2/1995 |
| WO | WO 95/09562 A1 | 4/1995 |
| WO | WO 96/05768 A1 | 2/1996 |
| WO | WO 97/10746 A1 | 3/1997 |
| WO | WO 97/25101 A2 | 7/1997 |
| WO | WO 97 29701 A1 | 8/1997 |
| WO | WO 97/29710 A1 | 8/1997 |
| WO | WO 98/24017 A2 | 6/1998 |
| WO | WO 98/49938 A1 | 11/1998 |
| WO | WO 99/16359 A1 | 4/1999 |
| WO | WO 99/33392 A1 | 7/1999 |
| WO | WO 99/51283 A2 | 10/1999 |
| WO | WO 99/59664 A1 | 11/1999 |
| WO | WO 00/10456 A1 | 3/2000 |
| WO | WO 00/27462 A1 | 5/2000 |
| WO | WO 00/54653 A1 | 9/2000 |
| WO | WO 00/74565 A1 | 12/2000 |
| WO | WO 01/49353 A2 | 7/2001 |
| WO | WO 01/67964 A2 | 9/2001 |
| WO | WO 01/70096 A1 | 9/2001 |
| WO | WO 01/70097 A1 | 9/2001 |
| WO | WO 01/74235 A1 | 10/2001 |
| WO | WO 01/80935 A1 | 11/2001 |
| WO | WO 02/24058 A2 | 3/2002 |
| WO | WO 02/39909 A1 | 5/2002 |
| WO | WO 02/47549 A1 | 6/2002 |
| WO | WO 02/064028 A1 | 8/2002 |
| WO | WO 02/068988 A1 | 9/2002 |
| WO | WO 02/069841 A2 | 9/2002 |
| WO | WO 02/089692 A1 | 11/2002 |
| WO | WO 02/096276 A1 | 12/2002 |
| WO | WO 03/028547 A2 | 4/2003 |
| WO | WO 03/073920 A2 | 9/2003 |
| WO | WO 03/073921 A1 | 9/2003 |
| WO | 03/086498 A2 | 10/2003 |
| WO | WO 03/092476 A2 | 11/2003 |
| WO | 2004/000403 A1 | 12/2003 |
| WO | WO 2004/006980 A2 | 1/2004 |
| WO | WO 2004/049905 A2 | 6/2004 |
| WO | WO 2004/071284 A1 | 8/2004 |
| WO | WO 2004/080313 A1 | 9/2004 |
| WO | WO 2004/084702 A1 | 10/2004 |
| WO | WO 2005/084542 A1 | 9/2005 |

OTHER PUBLICATIONS

Woodley et al; U.S. Appl. No. 11/871,104 entitled "System for managing bowden cables in articulating instruments," filed Oct. 11, 2007.

Berger, W. L. et al. Sigmoid Stiffener for Decompression Tube Placement in Colonic Pseudo-Obstruction. Endoscopy. 2000; 32 (1): 54-57.

Hasson, H.M. "Technique of open laparoscopy:equipment and technique. (from step 1 to step 9)." May 1979, 2424 North Clark Street, Chicago, IL 60614. 3 pages.

Lee, et al. A highly redundant robot system for inspection. Proceedings of Conference on Intelligent Robotics in Field, Factory, Service, and Space (CIRFFSS "94). Mar. 21-24, 1994. 1:142-148. Houston, Texas.

McKernan, et al. Laparoscopic general surgery. Journal of the Medical Association of Georgia. 1990; 79 (3):157-159.

Slatkin, et al. The development of a robotic endoscope. Proceedings 1995 IEEE/RSJ International Conference on Intelligent Robots and Systems. Aug. 5-9, 1995. 2:162-171. Pittsburgh, Pennsylvania.

Belson, Amir; U.S. Appl. No. 12/027,370 entitled "Apparatus and method for endoscopic colectomy," filed Feb. 7, 2008.

Durant et al.; U.S. Appl. No. 12/036,976 entitled "Systems and methods for articulating an elongate body," filed Feb. 25, 2008.

U.S. Appl. No. 09/556,673, filed Apr. 21, 2000, Francois et al.

Science & Technology, Laptop Magazine. Oct. 2002. p. 98.

European Search Report dated Jul. 6, 2012 for EP Application No. 05 71 2548.6.

Office Action issued in corresponding Japanese Application No. P2006-551580, Dispatch Date: Aug. 21, 2012, Dispatch No. 568236.

* cited by examiner

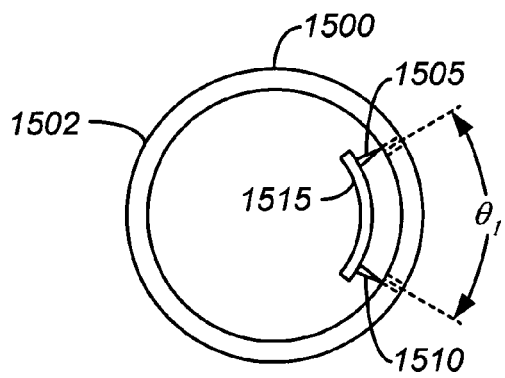
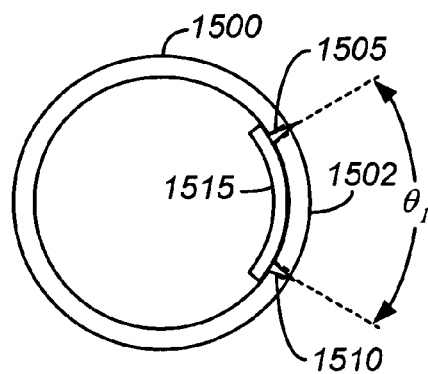
FIG. 15A  FIG. 15B
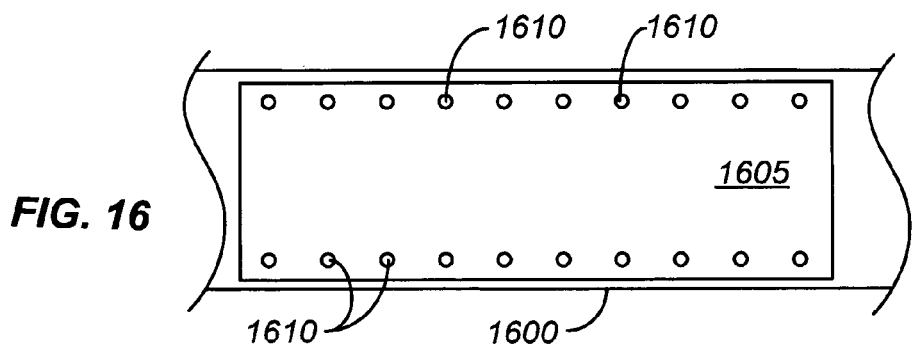
FIG. 16
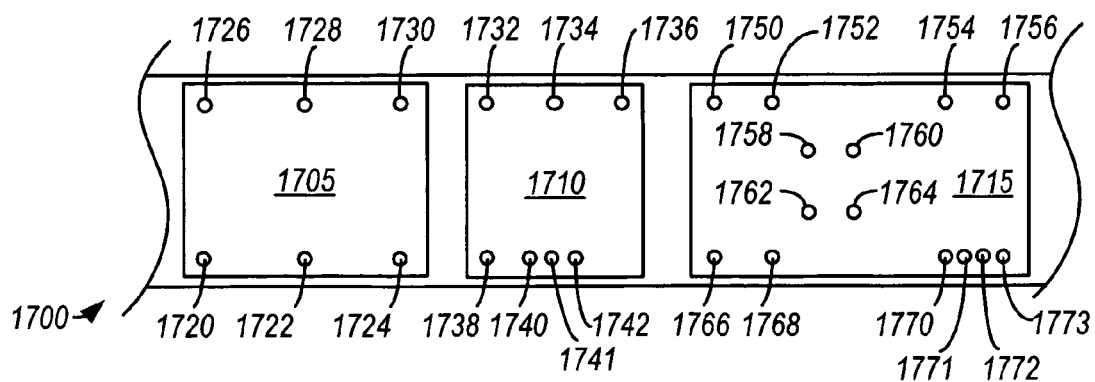
FIG. 17

APPARATUS AND METHODS FOR FACILITATING TREATMENT OF TISSUE VIA IMPROVED DELIVERY OF ENERGY BASED AND NON-ENERGY BASED MODALITIES

CROSS REFERENCE TO RELATED APPLICATIONS

This application claims priority to and is a Continuation-In-Part of application Ser. No. 10/767,109, filed Jan. 28, 2004 now abandoned, and of application Ser. No. 10/228,583, filed Aug. 26, 2002 now U.S. Pat No. 6,869,396, which is a Continuation of application Ser. No. 09/790,204, filed Feb. 20, 2001 (now U.S. Pat. No. 6,468,203) which claims priority to Provisional application Ser. No. 60/194,140, filed Apr. 3, 2000, each of which is incorporated herein by reference in its entirety for all purposes.

FIELD OF THE INVENTION

The present invention relates generally to endoscopes and endoscopic medical procedures. More particularly, it relates to methods and apparatus for accessing and treating regions within the body which are difficult to reach through conventional surgical devices and procedures.

BACKGROUND OF THE INVENTION

Many surgical procedures typically require large incisions be made to provide access to regions within the body. For instance, operating on or near the posterior regions of the heart is ordinarily performed using open-chest techniques. Such a procedure generally requires a gross thoracotomy or sternotomy, which are both highly invasive and attendant with a great deal of risks, such as ischemic damage to the heart, formation of emboli, etc. A thoracotomy typically involves creating an incision in the intercostal space between adjacent ribs while a sternotomy involves the "chest spreader" approach, which is generally the most invasive. Moreover, such an invasive procedure produces significant morbidity, increased mortality rates, and significantly increases recovery time for the patient.

Minimally invasive surgery is an alternative surgical procedure in which small incisions are made in the patient's body to provide access for various surgical devices for viewing and operating inside the patient. Laparoscopes are typically used for accessing and performing operations within the body through these small incisions using specially designed surgical instruments. These instruments generally have handles which are manipulatable from outside of the patient's body by the surgeon to control the operation of the instrument typically through an elongated tubular section which fits through a tube, introducer, or trocar device entering the patient's body.

However, even conventional laparoscopic procedures are limited in applicability in part because of a "straight-line" requirement in utilizing laparoscopic tools. This requirement makes accessing certain areas within the body extremely difficult, if not impracticable. Moreover, the lack of flexibility of these tools have made access to certain regions of the body difficult, forcing many surgeons to resort to open surgery rather than utilizing conventional minimally invasive procedures.

Flexible endoscopic devices are also available for use in minimally invasive surgical procedures in providing access to regions within the body. Flexible endoscopes are typically used for a variety of different diagnostic and interventional procedures, including colonoscopy, bronchoscopy, thoracoscopy, laparoscopy and video endoscopy. A flexible endoscope may typically include a fiberoptic imaging bundle or a miniature camera located at the instrument's tip, illumination fibers, one or two instrument channels that may also be used for insufflation or irrigation, air and water channels, and vacuum channels. However, considerable manipulation of the endoscope is often necessary to advance the device through the body, making use of conventional devices more difficult and time consuming and adding to the potential for complications.

Steerable flexible endoscopes have been devised to facilitate selection of the correct path though regions of the body. However, as the device is typically inserted farther into the body, it generally becomes more difficult to advance. Moreover, friction and slack in the endoscope typically builds up at each turn, making it more difficult to advance and withdraw the device. Another problem which may arise, for example, in colonoscopic procedures, is the formation of loops in the long and narrow tube of the colonoscope. Such loops may arise when the scope encounters an obstacle, gets stuck in a narrow passage, or takes on a shape that incorporates compound curves. Rather progressing, the scope forms loops within the patient. In an attempt to proceed in insertion of the colonoscope, for example, excess force may be exerted, damaging delicate tissue in the patient's body. The physician may proceed with the attempted insertion of the endoscope without realizing there is a problem.

Through a visual imaging device the user can observe images transmitted from the distal end of the endoscope. From these images and from knowledge of the path the endoscope has followed, the user can ordinarily determine the position of the endoscope. However, it is difficult to determine the endoscope position within a patient's body with any great degree of accuracy.

None of the instruments described above is flexible enough to address the wide range of requirements for surgical procedures performed internally to the patient's body. Furthermore, the instruments described lack the ability to rotate the distal tip about the longitudinal axis of the instrument while fully articulating the tip to any setting relative to the tubular section of the instrument. This lack of flexibility requires surgeons to manually rotate and move the instrument relative to the patient body to perform the procedure.

BRIEF SUMMARY OF THE INVENTION

Endoscopic devices, as described below, may be particularly useful in treating various regions within the body. Such endoscopes may include a steerable distal portion and an automatically controlled proximal portion which may be controlled by a physician or surgeon to facilitate steering the device while the proximal portion may be automatically controlled by, e.g., a controller or computer. The steerable endoscope may be advanced within the body of a patient, e.g., via any one of the natural orifices into the body such as through the anus. Alternatively, the device may be introduced percutaneously through a small incision into the body. Once the endoscopic device has been introduced into the body, it may be advanced and maneuvered to avoid obstructing anatomical features such as organs, bones, etc., without impinging upon the anatomy of the patient. Examples of such devices are described in detail in the following patents and co-pending applications: U.S. Pat. No.s 6,468,203; 6,610,007; U.S. patent application Ser. No. 10/087,100 filed Mar. 1; 2002; U.S. patent application Ser. No. 10/139,289 filed May 2, 2002, U.S. patent application Ser. No. 10/229,577 filed Aug.

27, 2002; U.S. patent application Ser. No. 10/229,814 filed Aug. 27, 2002, and U.S. patent application Ser. No. 10/306,580 filed Nov. 27, 2002, each of which is incorporated herein by reference in its entirety.

Using such a device, one method of treating an obstructed region of tissue within a body, may generally comprise advancing an elongate device into the body through an opening, the elongate device having a proximal portion and a selectively steerable distal portion and the elongate device having a plurality of segments, selectively steering the distal portion to assume a selected curve along a desired path within the body which avoids contact with tissue (or does not require displacement of adjacent tissue along the desired path or avoids applying excess force to the adjacent tissue), and further advancing the elongate device through the body and towards the region of tissue to be treated while controlling the proximal portion of the device to assume the selected curve of the distal portion.

Using any one of the controllable endoscopic devices, various regions of the body which are typically difficult to access and treat through conventional surgical techniques, may be accessed and treated accordingly. In one treatment variation, the endoscopic device may be utilized for neurological surgical applications. Because the endoscopic device is unconstrained by "straight-line" requirements for accessing regions of the brain which are conventionally difficult to reach and/or because the device avoids forming loops when advanced, the endoscope may be accurately advanced and positioned within the cranium by steering the device around the brain with minimal or no trauma to healthy brain tissue. The endoscope may also be advanced through the tissue as necessary to access treatment areas embedded deep within the tissue through pathways which may minimize any damage to healthy adjacent tissue. Furthermore, because the endoscopic device may allow access to sensitive regions over or within the brain, minimally invasive surgery may be performed where conventional surgery would normally require removal of portions of the skull, for instance, in craniotomy procedures or treatment of intracranial hematomas, etc. In addition, access through the nasal passages or other natural cranial orifices may be facilitated.

Another area of treatment in which the endoscopic device may be utilized may include use for coronary procedures, e.g., treatment of the mitral valve, tissue ablation for the treatment of atrial fibrillation, placement, removal, or adjustment of pacing leads, etc. In one example, the endoscopic device may be introduced within the heart via the superior vena cava and advanced through the right atrium. Once the endoscope is within the right atrium, the distal portion may be steered through the atrial septum and into the left atrium where the distal portion of the device may be positioned adjacent to the tissue to be treated, in this example, the mural valve. To affect treatment, various tools or devices, e.g., scalpels, graspers, etc., may be delivered through one or several working channel within the device to effect the treatment.

In yet another area of treatment in which the endoscopic device may be utilized, various thoracoscopy procedures may be accomplished in a minimally invasive procedure, e.g., percutaneously. As shown, the endoscope may be advanced into the patient via an introducer or port, which may also be configured as a datum for establishing a fixed point of reference for the endoscope during the procedure. The port or datum may be in electrical communication with a computer or processor used for determining and/or maintaining the position of the device within the patient. The endoscope may be advanced into the body of the patient through an incision made, e.g., in the intercostal space between the ribs. The endoscope may then be advanced into the thoracic cavity and maneuvered to regions within the body such as the posterior region of the heart which are normally inaccessible for conventional laparoscopic procedures due to a lack of straight-line access.

One embodiment of the present invention provides a method for facilitating a treatment within a body including inserting an endoscope having a steerable distal end and a controllable proximate end, the controllable proximate end being controlled to follow the steerable distal end. The endoscope is maneuvered into a position within the body to facilitate a treatment of a body portion. A treatment is performed on the body portion. The body portion could be, for example, in the thoracic cavity, the skull, or the peritoneal cavity.

Another embodiment of the present invention provides a system for performing a treatment of a condition related to a physiological indication within a body. There is a system for detecting and localizing a physiological indication within the body. A system for providing imaging of a portion of the body related to the physiological indication within the body. A steerable endoscope having a steerable distal end and a controllable proximate end under the control of a computer controller that receives information from the system for detecting and the system for providing.

Another embodiment of the present invention provides a system for facilitating a treatment of the heart having a system for indicating the location of an errant condition of the heart. There is also provided a controller system utilizing information generated by the system for indicating to assist in the articulation of a steerable endoscope having a steerable distal end and a controllable proximate end to follow the steerable distal end into a position to facilitate a treatment of the errant condition of the heart. In addition, there is provided a treatment device provided by the steerable endoscope to perform a treatment of the errant condition of the heart.

In another embodiment of the present invention, there is provided an apparatus for performing a cardiac ablation therapy having a steerable endoscope having a steerable distal end and a controllable proximate end configured to automatically follow the configuration of the steerable distal end. An ablation therapy device adapted to be deployed by the steerable endoscope. A fastener that fixes the position of the ablation therapy device.

Another embodiment of the present invention provides a method of performing a treatment within the body by advancing a steerable distal end of an endoscope along a pathway into a treatment position to facilitate a treatment within a body. The proximate end of the endoscope is controlled to follow the pathway of the steerable distal end of the endoscope. A treatment element is provided to the treatment position.

Another embodiment of the present invention utilizes a pair of steerable endoscopes to deliver a therapy within the body. The pair of endoscopes may be arranged such that one endoscope is within the other endoscope or, alternatively, where one endoscope is adjacent the other endoscope. In another embodiment, one steerable endoscope may be maneuvered into a desired position within the body to facilitate treatment and then fixed into that position. Thereafter, the second endoscope may be maneuvered to perform the therapy or facilitate a treatment utilizing the fixed position within the body provided by the first endoscope. This procedure may be useful in conditions of movement, such as beating heart treatments where the first endoscope may be used as a fixed treatment point for utilizing the second endoscope.

The endoscope device may also be utilized for procedures within the peritoneal cavity. Potential applications may include minimally invasive surgery for urologic, bariatric, and liver surgery. Moreover, minimally invasive access may be achieved for treatments in spinal or orthopedic surgery as well. In such a procedure, the endoscope may be introduced into the patient through an incision via a port, which may also function as a datum. The distal portion may be steered to avoid various organs while being advanced to a tissue region to be treated, e.g., the liver. The distal portion of the endoscope may accordingly be steered while the proximal portion may be automatically controlled to follow a path defined by the distal portion which minimizes contact with the surrounding and adjacent tissue and organs. In this or any other procedure, one or more laparoscopes may optionally be used in combination with the endoscope to assist with the surgical procedure.

BRIEF DESCRIPTION OF THE DRAWINGS

FIGS. 15A and 15B show an embodiment of a needle array in a retracted (FIG. 15A) and a deployed (FIG. 15B) configuration.

FIG. 16 shows an embodiment of a needle array having a continuous spacing.

FIG. 17 shows an embodiment of a needle array having a variety of spacing configurations.

DETAILED DESCRIPTION OF THE INVENTION

In treating various regions within the body, a number of different endoscopic devices may be utilized in facilitating access. Endoscopic devices which are particularly useful may include various endoscopes having a steerable distal portion and an automatically controlled proximal portion. Generally, the steerable distal portion may be controlled by a physician or surgeon to facilitate steering the device while the proximal portion may be automatically controlled by, e.g., a controller or computer. The steerable endoscope may be advanced within the body of the patient through a number of different methods. For instance, the endoscope may be introduced via any one of the natural orifices into the body such as through the anus. Alternatively, the device may be introduced percutaneously through a small incision into the body. Once the endoscopic device has been introduced into the body, it may be advanced and maneuvered, as described below, to avoid obstructing anatomical features such as organs, bones, etc., without impinging upon the anatomy of the patient.

Figure 1:
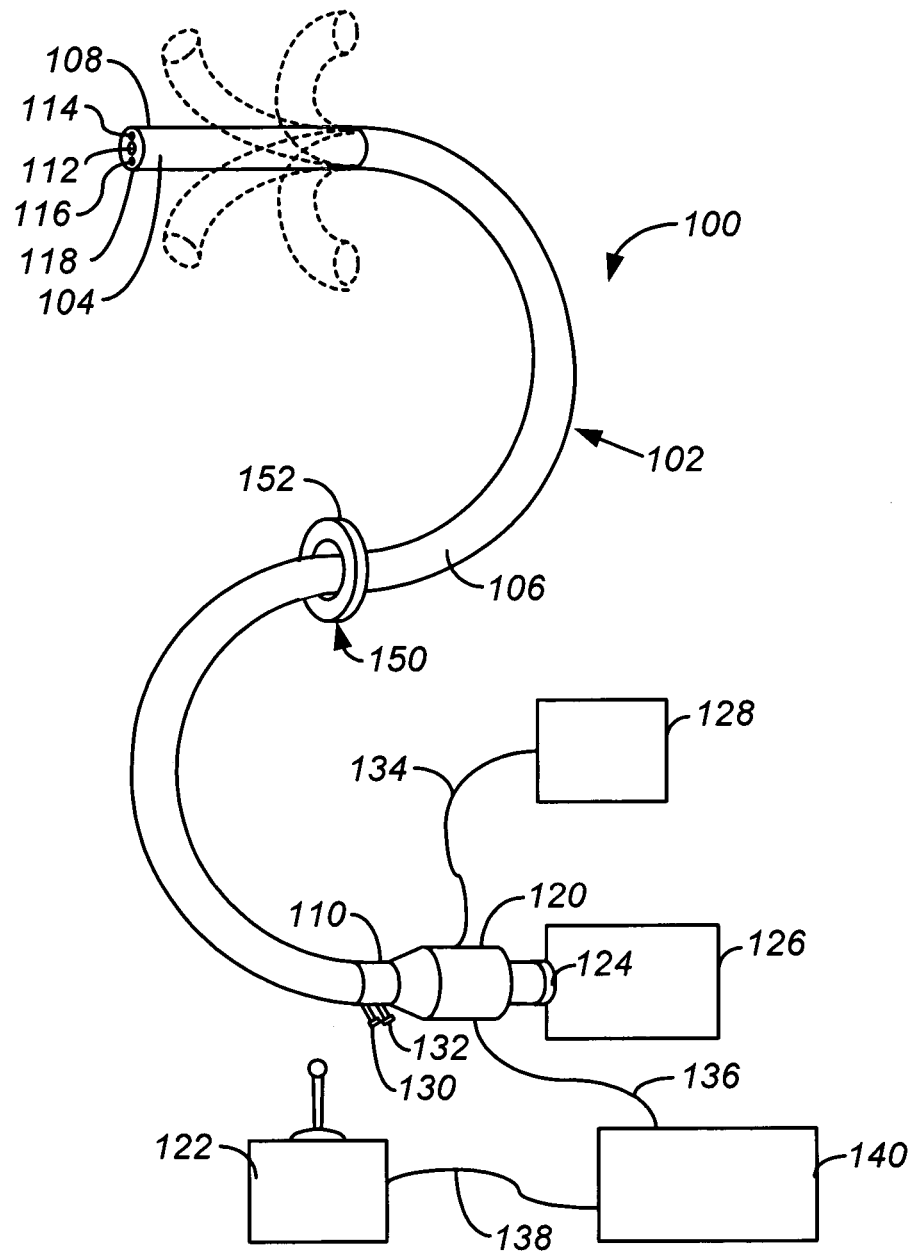
FIG. 1 shows one variation of a steerable endoscope which may be utilized for accessing various regions within the body without impinging upon the anatomy of the patient.

FIG. 1 illustrates one variation of a steerable endoscope 100 which may be utilized for accessing various regions within the body without impinging upon the anatomy of the patient. The endoscope 100 generally has an elongate body 102 with a manually or selectively steerable distal portion 104 and an automatically controlled proximal portion 106. The selectively steerable distal portion 104 may be selectively steered or bent up to a full 180° bend in any direction, as shown by the dashed lines. A fiberoptic imaging bundle 112 and one or more illumination fibers 114 may optionally be extended through the body 102 from the proximal end 110 to the distal end 108. Alternatively, the endoscope 100 may be configured as a video endoscope with a miniaturized video camera, such as a CCD or CMOS camera, positioned at the distal end 108 of the endoscope body 102. The images from the video camera may be transmitted to a video monitor by a transmission cable or by wireless transmission. Optionally, the body 102 of the en doscope 100 may also include at least one or two instrument channels 116, 118 that may be used to provide access through the endoscope for any number of tools. Channels 116, 118 may also be used for various other purposes, e.g., insufflation or irrigation.

The elongate body 102 of the endoscope 100 is highly flexible so that it is able to bend around small diameter curves without buckling or kinking. The elongate body 102 of the endoscope 100 may range in length typically from, e.g., 135 to 185 cm, and 12 to 13 mm in diameter. However, if the endoscope 100 were utilized in regions within the body which are smaller than the space within, e.g., the gastrointestinal tract, the device may be modified in size to be smaller in diameter. The endoscope 100 may also be modified in length to be longer or shorter, depending upon the desired application.

A handle 120 is attachable to the proximal end 110 of the elongate body 102. The handle 120 may include an ocular 124 connected to the fiberoptic imaging bundle 112 for direct viewing and/or for connection to a video camera 126. The handle 120 may also be connected to an illumination source 128 via an illumination cable 134 that may connected to or continuous with the illumination fibers 114. An optional first luer lock fitting 130 and an optional second luer lock fitting 132, which may be in communication with instrument channels 116, 118, respectively, may also be located on or near the handle 120.

The handle 120 may be connected to an electronic motion controller 140 by way of a controller cable 136. A steering control 122 may be connected to the electronic motion controller 140 by way of a second cable 138. The steering control 122 may be configured to allow the physician or surgeon to selectively steer or bend the selectively steerable distal portion 104 of the elongate body 102 in the desired direction. The steering control 122 may be a joystick controller as shown, or other known steering control mechanism. Alternatively, the steering may be effected manually, e.g. by the use of cables, hydraulics, or pneumatics, or any other known mechanical apparatus for controlling the distal portion of the elongate body. The electronic motion controller 140 may be used to control the motion of the automatically controlled proximal portion 106 of the elongate body 102 and may be implemented using a motion control program running on a microcomputer or through an application-specific motion controller. Alternatively, the electronic motion controller 140 may be implemented using a neural network controller.

An axial motion transducer 150 may be provided to measure the axial motion of the elongate body 102 as it is advanced and withdrawn. The axial motion transducer 150 can be made in many configurations, some of which are described below. In this variation, the axial motion transducer 150 is configured as a ring 152, for illustrative purposes only, that surrounds the elongate body 102 of the endoscope 100. The axial motion transducer 150 may be attached to a fixed point of reference, such as the surgical table or the insertion point for the endoscope 100 on the patient's body, as described below. As the body 102 of the endoscope 100 slides through the axial motion transducer 150, it produces a signal indicative of the axial position of the endoscope body 102 with respect to the fixed point of reference and sends a signal to the electronic motion controller 140 by telemetry or by a cable (not shown). The axial motion transducer 150 may use optical, electronic, magnetic, mechanical, etc., methods to determine the axial position of the endoscope body 102. In addition, the motion transducer may be configured to simultaneously measure and communicate rotational motion of the endoscope, so that this additional data may be used in the control of the instrument's motion. A further detailed description for the axial motion transducer 150 and variations thereof may be found in U.S. patent application Ser. No. 10/384,252 filed Mar. 7, 2003, which is incorporated herein by reference in its entirety.

Figure 2A:
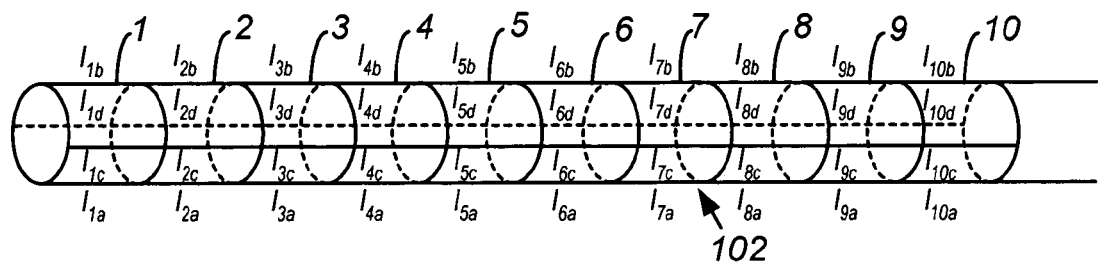
FIG. 2A shows a wire frame model of a section of the elongate body of the endoscope in a neutral or straight position.

To illustrate the basic motion of the steerable endoscope 100, FIG. 2A shows a wire frame model of a section of the body 102 of the endoscope 100 in a neutral or straight position. Most of the internal structure of the endoscope body 102 has been eliminated in this drawing for the sake of clarity. The endoscope body 102 is divided up into sections 1, 2, 3 . . . 10, etc. The geometry of each section is defined by four length measurements along the a, b, c and d axes. For example, the geometry of section 1 may be defined by the four length measurements $1_{1a}$, $1_{1b}$, $1_{1c}$, $1_{1d}$, and the geometry of section 2 may be defined by the four length measurements $1_{2a}$, $1_{2b}$, $1_{2c}$, $1_{2d}$, etc. The geometry of each section may be altered using the linear actuators to change the four length measurements along the a, b, c and d axes. For example, to bend the endoscope body 102 in the direction of the a axis, the measurements $1_{1a}$, $1_{2a}$, $1_{3a}$ . . . $1_{10a}$ can be shortened and the measurements $1_{1b}$, $1_{2b}$, $1_{3b}$ . . . $1_{10b}$ can be lengthened an equal amount. The amount by which these measurements are changed determines the radius of the resultant curve. In the automatically controlled proximal portion 106, however, the a, b, c and d axis measurements of each section may be automatically controlled by the electronic motion controller 140.

Figure 2B:
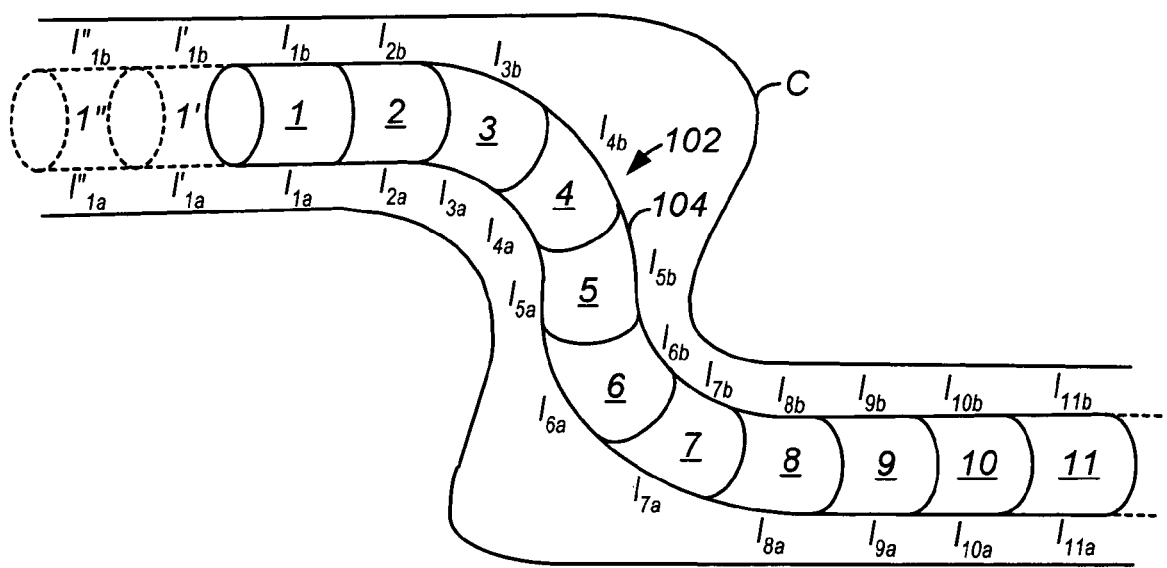
FIG. 2B shows an illustration of the endoscope body maneuvered through a curve with the selectively steerable distal portion and automatically controlled proximal portion.

In FIG. 2B, the endoscope body 102 has been maneuvered through the curve C with the benefit of the selectively steerable distal portion 104 and now the automatically controlled proximal portion 106 resides in the curve C. Sections 1 and 2 are in a relatively straight part of the curve C, therefore $1_{1a}=1_{1b}$ and $1_{2a}=1_{2b}$. However, because sections 3-7 are in the S-shaped curved section, $1_{3a}<1_{3b}$, $1_{4a}<1_{4b}$ and $1_{5a}<1_{5b}$, but $1_{6a}>1_{6b}$, $1_{7a}>1_{7b}$ and $1_{8a}>1_{8b}$. When the endoscope body 102 is advanced distally by one unit, section 1 moves into the position marked 1', section 2 moves into the position previously occupied by section 1, section 3 moves into the position previously occupied by section 2; etc. The axial motion transducer 150 produces a signal indicative of the axial position of the endoscope body 102 with respect to a fixed point of reference and sends the signal to the electronic motion controller 140. Under control of the electronic motion controller 140, each time the endoscope body 102 advances one unit, each section in the automatically controlled proximal portion 106 is signaled to assume the shape of the section that previously occupied the space that it is now in. Therefore, when the endoscope body 102 is advanced to the position marked 1', $1_{1a}=1_{1b}$, $1_{2a}=1_{2b}$, $1_{3a}=1_{3b}$, $1_{4a}<1_{4b}$, $1_{5a}<1_{5b}$, $1_{6a}<1_{6b}$, $1_{7a}>1_{7b}$, $1_{8a}>1_{8b}$, and $1_{9a}>1_{9b}$, and, when the endoscope body 102 is advanced to the position marked 1", $1_{1a}=1_{1b}$, $1_{2a}=1_{2b}$, $1_{3a}=1_{3b}$, $1_{4a}=1_{4b}$, $1_{5a}<1_{5b}$, $1_{6a}<1_{6b}$, $1_{7a}<1_{7b}$, $1_{8a}>1_{8b}$, $1_{9a}>1_{9b}$, and $1_{10a}>1_{10b}$. Thus, the S-shaped curve propagates proximally along the length of the automatically controlled proximal portion 106 of the endoscope body 102. The S-shaped curve appears to be fixed in space, as the endoscope body 102 advances distally.

Similarly, when the endoscope body 102 is withdrawn proximally, each time the endoscope body 102 is moved proximally by one unit, each section in the automatically controlled proximal portion 106 is signaled to assume the shape of the section that previously occupied the space that it is now in. The S-shaped curve propagates distally along the length of the automatically controlled proximal portion 106 of the endoscope body 102, and the S-shaped curve appears to be fixed in space, as the endoscope body 102 withdraws proximally.

Whenever the endoscope body 102 is advanced or withdrawn, the axial motion transducer 150 may be used to detect the change in position and the electronic motion controller 140 may be used to propagate the selected curves proximally or distally along the automatically controlled proximal portion 106 of the endoscope body 102 to maintain the curves in a spatially fixed position. Similarly, if the endoscope 102 is rotated, a rotational motion transducer (separate from or integrated within transducer 150) may be used to detect the change in position and the electronic motion controller may be similarly used to adjust the shape of the endoscope body 102 to maintain the curves in a spatially fixed position. This allows the endoscope body 102 to move through tortuous curves without putting unnecessary force on the wall of the curve C.

Examples of other endoscopic devices which may be utilized in the present invention are described in further detail in the following patents and co-pending applications, U.S. Pat. Nos. 6,468,203; 6,610,007; U.S. patent application Ser. No. 10/087,100 filed Mar. 1, 2002; U.S. patent application Ser. No. 10/139,289 filed May 2, 2002, U.S. patent application Ser. No. 10/229,577 filed Aug. 27, 2002; U.S. patent application Ser. No. 10/229,814 filed Aug. 27, 2002, and U.S. patent application Ser. No. 10/306,580 filed Nov. 27, 2002, each of which has been incorporated herein by reference above.

Therefore, using any one of the controllable endoscopic devices described above, various regions of the body which are typically difficult to access and treat through conventional surgical techniques, may be accessed and treated accordingly. In one treatment variation, the endoscopic device may be utilized for neurological surgical applications. Because the endoscopic device is unconstrained by "straight-line" requirements for accessing regions of the brain which are conventionally difficult to reach, the endoscope may be advanced and positioned within the cranium by steering the device around the brain with minimal or no trauma to healthy brain tissue. The endoscope may also be advanced through the tissue as necessary to access treatment areas embedded deep within the tissue through pathways which may minimize any damage to healthy adjacent tissue. Furthermore, because the endoscopic device may allow access to sensitive regions over or within the brain, minimally invasive surgery may be performed where conventional surgery would normally require removal of portions of the skull, for instance, in craniotomy procedures or treatment of intracranial hematomas, etc.

Figure 3:
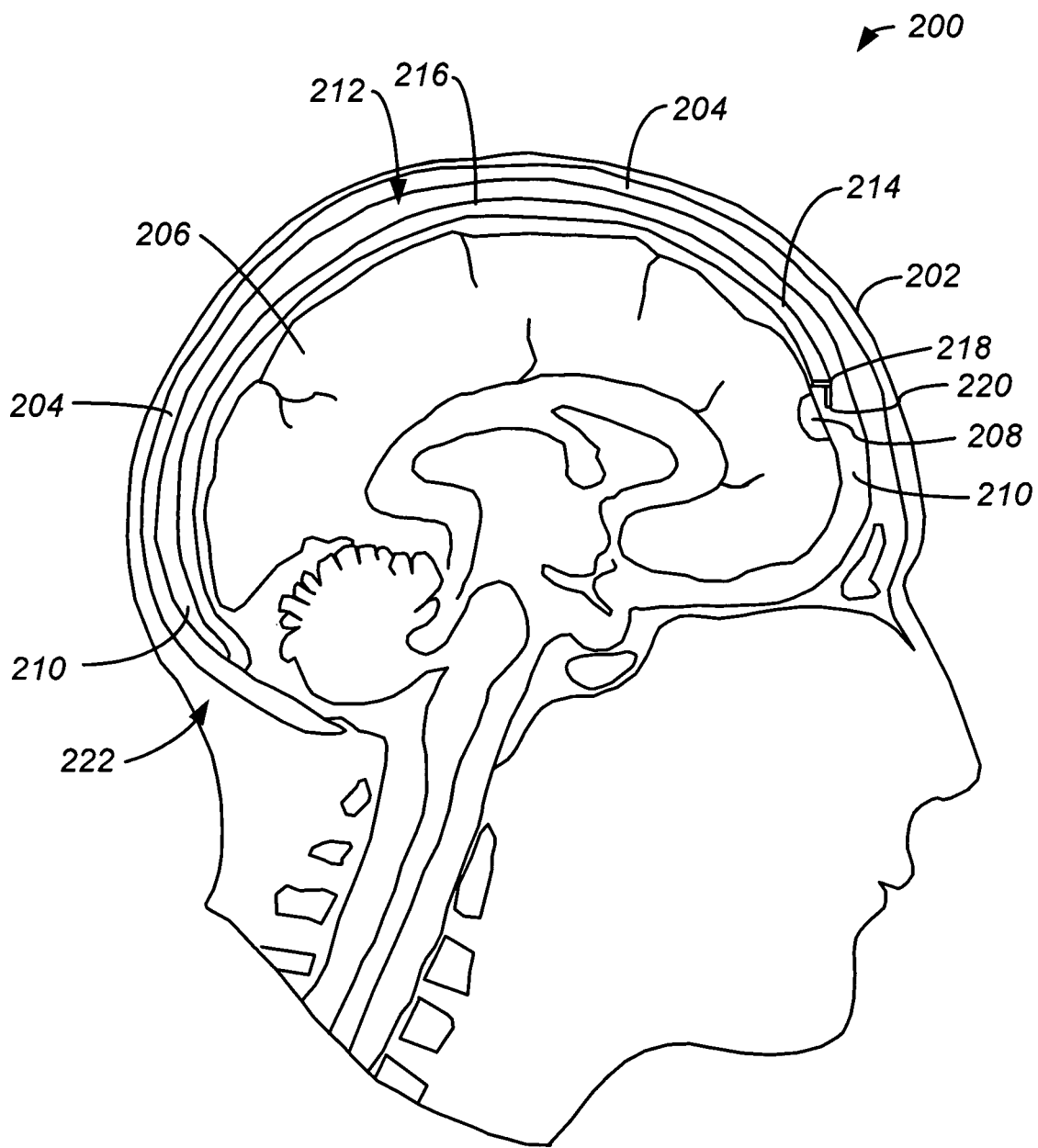
FIG. 3 shows a cross-sectional side view of a patient's head with a variation of the endoscope being advanced therethrough.

FIG. 3 shows a cross-sectional side view of head 202 of patient 200. The brain 206 may be seen within the cranial cavity 210 of cranium 204. The endoscopic device 212 is an embodiment of a steerable endoscope of the present invention that has been sized, shaped and configured for accessing the interior of the cranial cavity and external and internal regions of the brain. The movement, position, tracking and control of the endoscopic device 212 is performed by a user alone or in cooperation with any or all of imaging systems, position and location systems, and surgical planning methods and techniques. In treating regions of the brain 206 which may be difficult to normally access, the endoscopic device 212 may be introduced into the cranial cavity 210 from an easily accessible insertion site 222, e.g., a perforation within the skull. The endoscope 212 may be then advanced through the insertion site 222 by controlling the steerable distal portion 214 to avoid brain tissue. As the endoscope 212 is further advanced into the cranial cavity 210, the automatically controlled proximal portion 216 may attain the shape defined by the steerable distal portion 214 to avoid contact with brain tissue 206.

The endoscope 212 may be further advanced through the cranial cavity 210 and within the cerebrospinal fluid so that the device is advanced above or within the layers of the meninges, e.g., within the subarachnoid space. In either case, the endoscope 212 may be steered along a path which avoids or minimizes contact or pressure against the brain tissue 206. As the controlled proximal portion 216 is advanced distally and attains the shape defined by the distal portion 214, the proximal portion 216 likewise may be controlled to automatically avoid or minimize contact or pressure against the brain tissue 206. Once the distal portion 216 is advanced to the desired treatment region 208, various tools 220 may be introduced through the instrument channel 218 to enable treatment of the region 208. Any number of treatments or procedures may accordingly be effected, e.g., tumor biopsy and/or removal, shunt placement, lead placement, device placement, drainage of excess cerebrospinal fluid or blood, etc.

Figure 4:
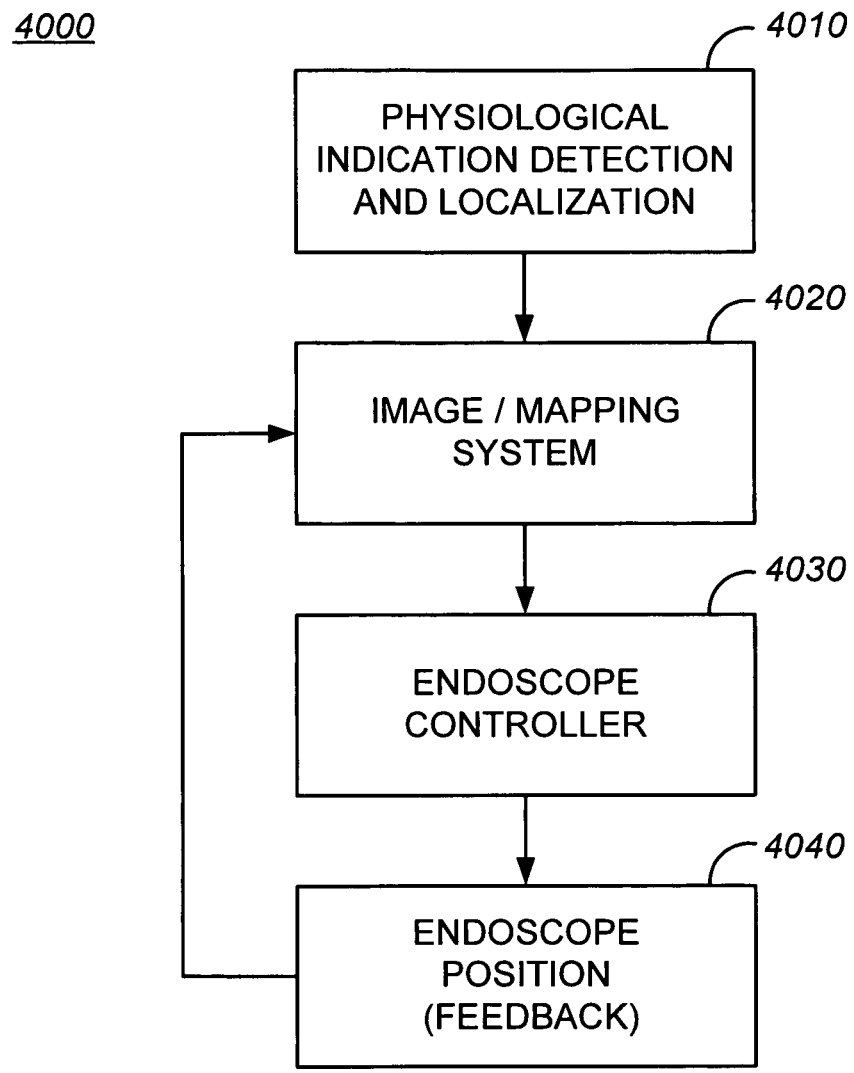
FIG. 4 shows the interaction of several components to provide a method of positioning a steerable endoscope system to facilitate treatment.

FIG. 4 shows the interaction of several components to provide a method of positioning a steerable endoscope system to facilitate treatment. As mentioned above, the movement, position, tracking and control of endoscopic devices according to the present invention is performed by a user alone or in cooperation with any or all of imaging systems, position and location systems, and surgical planning methods and techniques. The system schematic 4000 illustrates one embodiment of an integrated detection, mapping and control system for positioning and controlling a steerable, controllable endoscope of the present invention. First, a suitable device, element or system is used to detect and localize a physiological indication (4010). A physiological indication could be any perceptible indicia of a condition for which treatment may be facilitated. In an coronary example, physiological indicators include electrophysiology data or electrical signals from the heart. This system would be capable of identifying or performing analysis of monitored data to identify or determine the location of errant activity.

Next, information regarding the detected and localized physiological indication is passed to an image/mapping system (4020). An image/mapping system includes any imaging modality that may provide position, location, tissue type, disease state, or any other information that facilitates correlating the physiological activity to a identifiable and/or localizable position within the anatomy or within a frame of reference. Examples of image/mapping systems include any of the imaging technologies such as x-ray, fluoroscopy, computed tomography (CT), three dimensional CAT scan, magnetic resonance imaging (MRI), and magnetic field locating systems. Examples of image/mapping systems specifically suited for the treatment of cardiovascular disorders include electrocardiogram detection systems, cardiac electrophysiology mapping systems, endocardial mapping systems, or other systems and methods that provide the ability acquire, visualize, interpret and act on cardiac electrophysiological data. An example of such a system is described in U.S. Pat. No. 5,848,972 entitled, "Method for Endocardial Activation Mapping Using a Multi-Electrode Catheter" the entirety of which is incorporated herein by reference. Additional examples are described in U.S. Pat. Nos. 5,487,385; 5,848,972; and 5,645,064, the entirety of each of these patents is incorporated by reference. Integrated mapping, detection and/or ablation probes and devices may also be delivered using the steerable endoscope of the present invention. One such integrated system is described in US Patent Application Publication US 2003/0236455 to Swanson et al the entirety of which is incorporated herein by reference. Additional other systems may provide mapping, display or position information of a local isochronal activation map of the heart along with the relative position of the endoscope and direction information or movement commands to position the endoscope (or components, elements or systems onboard the endoscope) to provide treatment to the source of the arrhythmia.

Next, information provided, compiled and/or analyzed in the prior steps or other additional information provided by a user or other system used by the user is input into or utilized by the endoscope controller (4030). This step indicates the ability of the endoscope controller to respond to the indication, position, image, mapping and other data and utilize that data for altering the scope configuration, position, orientation or other relational information indicative of the scope controller responding to the information provided. The endoscope is configured to provide of facilitate providing components, elements or systems to facilitate a treatment of the physiological indication being monitored. The controller utilizes the data provided to position the steerable, controllable endoscope into a position related to the location or site that exhibits the errant activity. The proximity of the endoscope to the location or site of the errant activity will vary depending upon, for example, the treatment being implemented, the element, component or system being used to facilitate treatment.

Finally, the position of the endoscope is supplied back into the image or mapping system as a form of feedback to better assist in guiding the endoscope into the desired position to facilitate treatment (4040).

In another embodiment, the system 4000 may include an overall mapping system that provides medically significant data that facilitates a treatment. This overall mapping or imaging system may include mapping or imaging an area of monitored activity. The area of monitored activity includes not only the portion of the body important to the treatment but also imaging information of those other parts of the body not impacted by the treatment but are instead the likely pathway (s) of the steerable, controllable endoscope to reach the area where the treatment will be facilitated. In addition, some embodiments of the system may include the ability to detect, localize or otherwise indicate the position of the treatment area or area of errant activity or conditions subject to treatment. These indications may then be utilized to augment the guidance of the steerable, controllable endoscope into the desired position to facilitate treatment. In addition, other medical imaging and tracking systems may be utilized to provide tracking, guidance and position feedback information to the control of the steerable endoscope. An exemplary system is described by Dumoulin et al. in U.S. Pat. No. 5,377,678 which is incorporated herein by reference in its entirety.

The above steps are only representative of one embodiment of how physiological indications, and position information may be utilized to improve the guidance system and controls used by steerable endoscopes to ensure the placement of the endoscope to facilitate treatment. It is to be appreciated that the steps were utilized for clarity and ease of discussion. The methods of embodiments of the invention are not so limited. For example, a single system could be used as an integrated indication, imaging, endoscope controller that receives endoscope position feedback in real time. In an alternative example, the physiological indication and image/mapping functions may be combined into a single unit. As such, while the above steps have been described as happening only once or in a serial fashion, it is to be appreciated that the steps may be conducted in as different order or multiple times. Other physiological indication detection and localization systems may be used and will correspond to an appropriate system useful in the treatment being performed. In addition, alternative image and mapping systems may also be employed and may also be selected depending upon the treatment being facilitated through the use of a steerable controllable endoscope of the present invention. The system may also control the movement of the endoscope automatically based on inputs from the user, pre-surgical planning data, or other indications of desired pathways or pathways to avoid. Alternatively, or in addition, a user may input additional guidance or control information into the system for furthering the guidance or desired placement of the endoscope.

Another area of treatment in which the endoscopic device may be utilized may include use for coronary procedures, e.g., treatment of the mitral valve, performing or facilitating treatment of supraventricular tachycardia, including, for example, tissue ablation for the treatment of atrial fibrillation, treatment of ventricular tachycardia alone or in combination with treatment of supraventricular tachycardia, treatments for the placement, repositioning or removal of device leads, etc. Atrial fibrillation is typically sustained by the presence of multiple electrical reentrant wavelets propagating simultaneously in the atria of the heart. Surgical and catheter-based techniques typically place segmented or continuous lesions near and around the pulmonary veins as one way to re-synchronize the atria.

In addition, a variety of ablation techniques using energy based and non-energy based modalities may be utilized to ablate soft tissue. Embodiments of the present invention may be utilized to facilitate ablation therapies, ablation elements and devices that employ one or a combination of energy modalities, such as, for example, cryogenic energy, hydraulic energy, laser energy, magnetic energy, mechanical energy, microwave energy, radiation energy, radio-frequency energy, thermal energy, and ultrasonic energy. Microwave ablation systems may include, for example, those based on AFx microwave surgical ablation systems such as the AFx Flex 4 or the like. AFx is currently owned by Guidant Corp. Cryogenic ablation systems may include, for example, systems available from Cryocath Technologies such as the "SurgiFrost," "Frostbyte" or "Artic Circler" systems and the like. Ultrsound based surgical probes may be, for example, based upon the ultrasound ablation systems produced by EpiCor Medical or the like. A large number of commercially available ablation systems are available to illustrate the wide variety of ablation systems, techniques and modalities that may be delivered or utilized by embodiments of the steerable endoscopic systems of the present invention.

Figure 5:
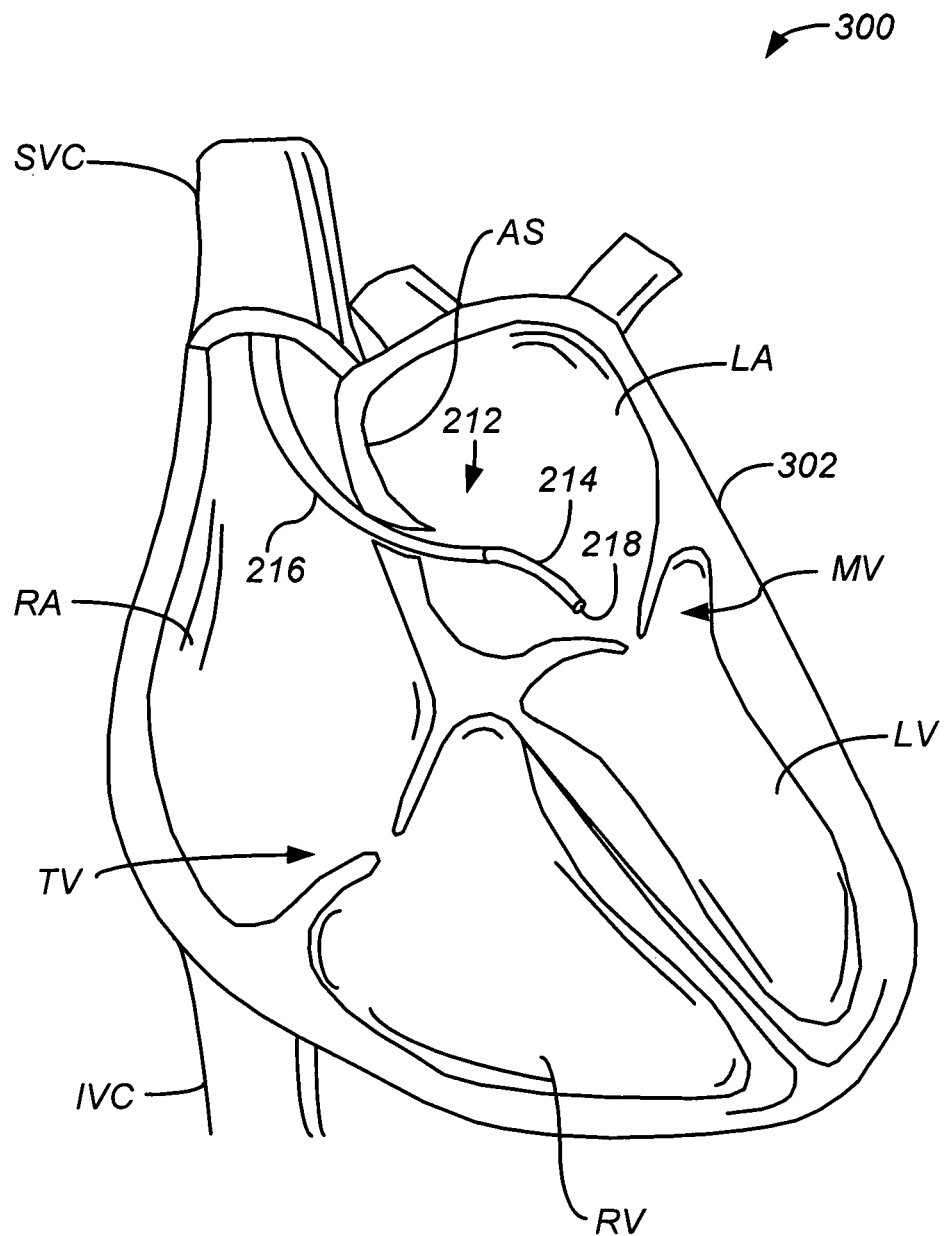
FIG. 5 shows a cross-sectional anterior view of a heart with the endoscopic device introduced via the superior vena cava and advanced to the right atrium.

As shown in FIG. 5, a cross-sectional anterior view of heart 302 may be seen in coronary procedure 300 for treatment of the mitral valve MV located between the left atrium LA and the left ventricle LV. The endoscopic device 212 is shown in this treatment variation as being introduced within the heart 302 via the superior vena cava SVC and advanced through the right atrium RA. Also shown is the right ventricle RV below the tricuspid valve TV and inferior vena cava IVC. The endoscope 212 may be sized accordingly to be delivered intravascularly. Once the endoscopic device 212 is within the right atrium RA, the distal portion 214 may be steered towards the atrial septum AS which separates the left atrium LA and right atrium RA. Once at the atrial septum AS, a cutting tool deliverable through the device 212 may be used to perforate the atrial septum AS to allow passage of the endoscopic device 212 into the left atrium LA. The distal portion 214 may then be steered and positioned adjacent the mitral valve MV while the proximal portion 216 is automatically controlled to minimize any pressure which may be exerted by the device 212 against the tissue of the heart 302. Once the endoscopic device is adjacent to the tissue to be treated, in this example the mitral valve MV, various tools or devices may be delivered through the channel 218 to effect the treatment. Once the procedure has been completed, the endoscope 212 may simply be withdrawn proximally in the same manner while minimizing any contact pressure against the tissue.

Figure 6:
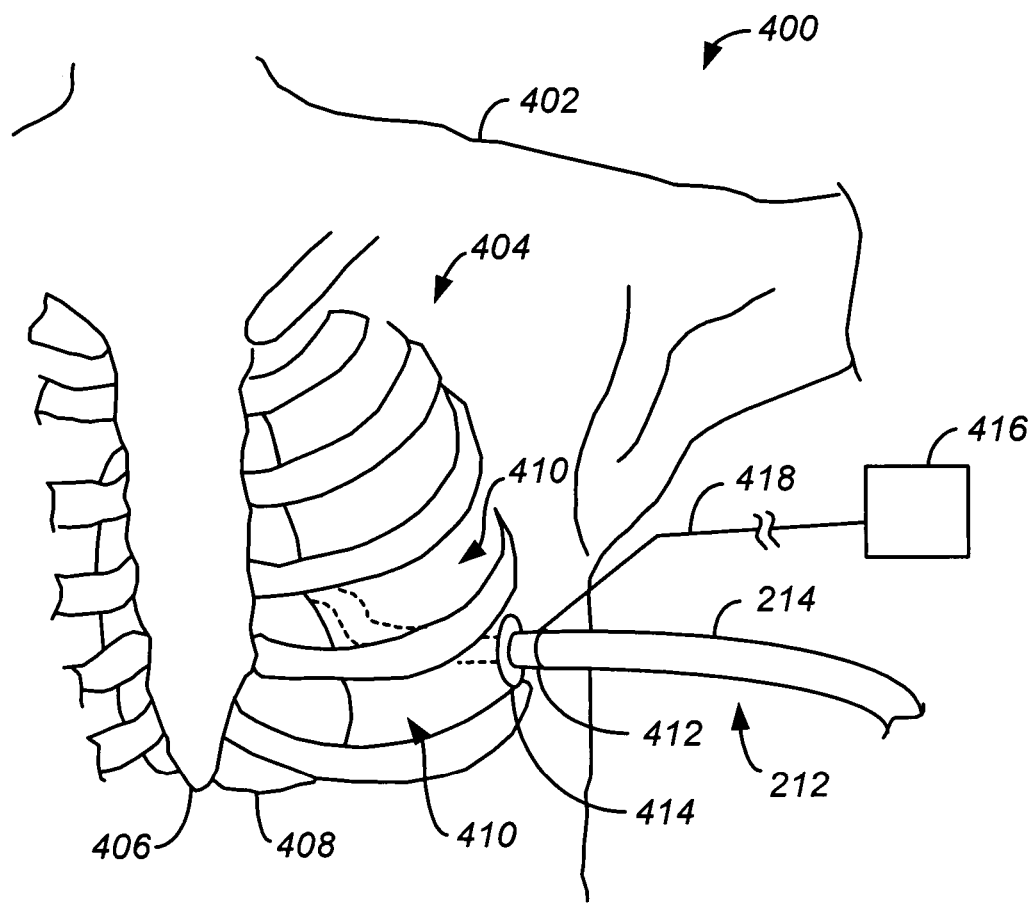
FIG. 6 shows an example of a thoracoscopy procedure which may be performed percutaneously with the endoscopic device.

In yet another area of treatment in which the endoscopic device may be utilized, various thoracoscopy procedures may be accomplished in a minimally invasive procedure. FIG. 6 shows an example of a thoracoscopy procedure 400 which may be performed percutaneously. As shown, the endoscope 212 may be advanced into the patient 402 via an introducer or port 412, which may also be configured as a datum for establishing a fixed point of reference for the endoscope 212 during the procedure. The port or datum 412 may be in electrical communication via electrical lines 418 with a computer or processor 416 which may be used for determining and/or maintaining the position of the device 212 within the patient 402. The endoscope 212 may be advanced into the body of the patient 402 through an incision 414 made, e.g., in the intercostal space between the ribs 404. The endoscope 212 may then be advanced into the thoracic cavity and maneuvered to regions within the body such as the posterior region of the heart 408 which are normally inaccessible for conventional laparoscopic procedures due to a lack of straight-line access.

In this example, the endoscopic device 212 is shown having been inserted through port or datum 412 and advanced posteriorly of heart 408 behind sternum 406. The lungs are not shown for the sake of clarity; however, the endoscope 212 may be steered and advanced around the lungs in a manner described above so as to avoid contact or to minimize contact with the lung tissue or any other organs or structures which may be obstructing a straight-line path.

The endoscopic device 212 is capable of reaching regions within the body, without damaging surrounding tissue, which is normally inaccessible via conventional laparoscopic procedures. FIGS. 7A to 7D show an example of the endoscopic device advanced about the posterior region of a heart to facilitate treatment of a supraventricular tachycardia. One example of a supraventricular tachycardia is atrial fibrillation. Another procedure 500 is shown in FIGS. 7A to 7D, which illustrate how the endoscopic device may be utilized for the treatment of atrial fibrillation. The figures show a posterior view of the heart with the aorta AA and pulmonary trunk PT as anatomical landmarks. Atrial fibrillation is typically sustained by the presence of multiple electrical reentrant wavelets propagating simultaneously in the atria of the heart. Surgical and catheter-based techniques typically place segmented or continuous lesions near and around the pulmonary veins as one way to re-synchronize the atria.

Figure 7A:
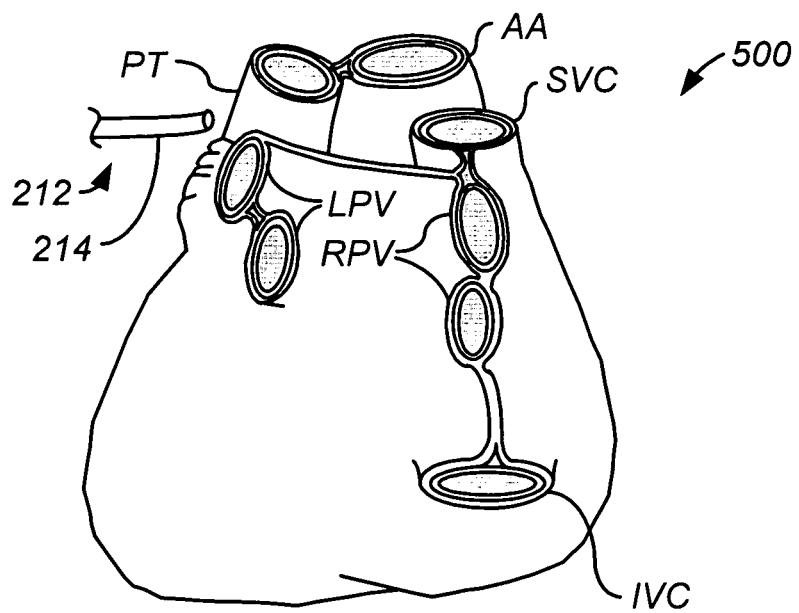
FIGS. 7A to 7D show an example of the endoscopic device advanced about the posterior region of a heart to facilitate treatment of a supraventricular tachycardia.
Figure 7B:
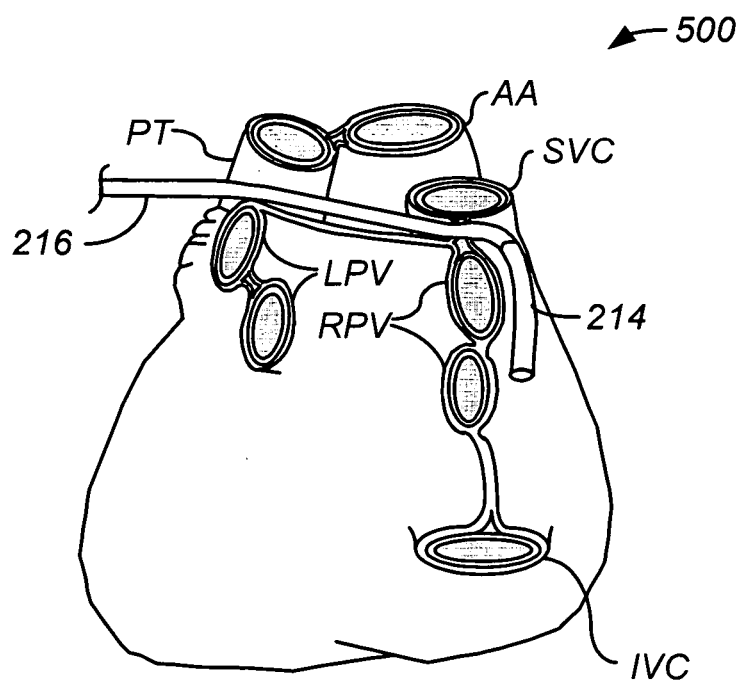
Figure 7C:
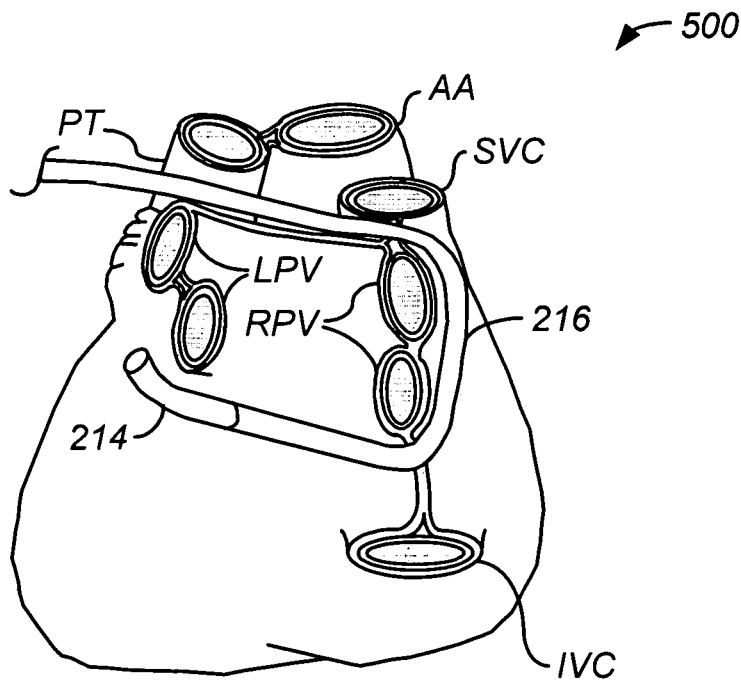
Figure 7D:
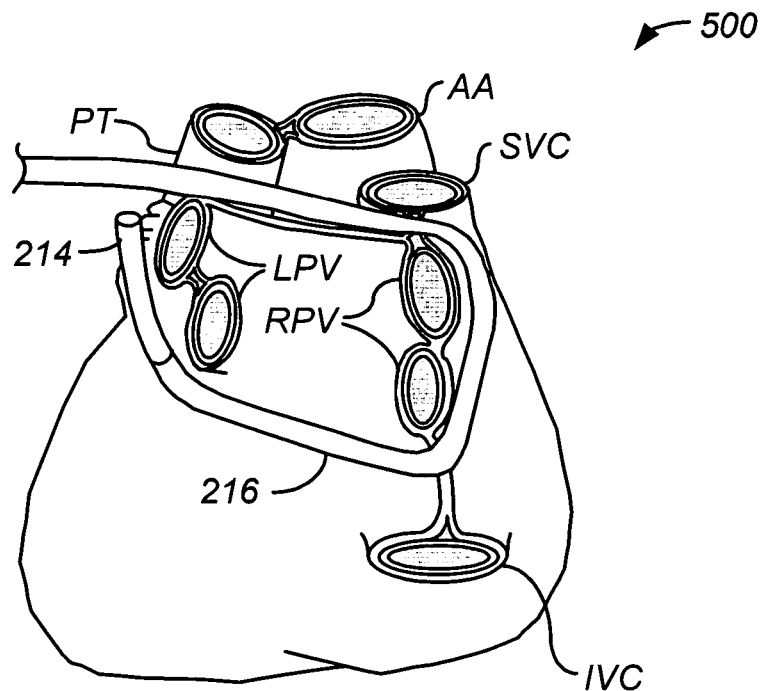

The endoscopic device 212 may be utilized by advancing the device 212 into the thoracic cavity, as described above or through various other channels, and steered towards the posterior region of the heart. In the example shown in FIGS. 7A to 7D, the steerable distal portion 214 may be advanced as shown in FIG. 7A such that the endoscope 212 approaches above the left pulmonary veins LPV. As shown in FIG. 7B, the distal portion 214 may be steered around the right pulmonary veins RPV while the endoscope 212 is advanced distally. The automatically controllable proximal portion 216 may thus assume the shape defined by the distal portion 214 in traversing around the pulmonary vessels. As shown in FIG. 7C, the distal portion 214 is steered around the left pulmonary vessels LPV while the proximal portion has assumed the curved path traversed by the device around the right pulmonary vessels RPV. Finally in FIG. 7D, the device 212 may be fully advanced entirely around the pulmonary vessels such that the distal portion 214 and proximal portion 216 are in intimate contact against the heart tissue while maintaining its configuration. The tissue which is in contact against the device 212 may then be ablated by one or several electrodes located along the length of the distal and/or proximal portions 214, 216, as described in further detail below. Alternately, an ablation device such as a catheter or other energy source, may be delivered through one or more working channels in or on the endoscope, and left in place as desired. This ablation device may then be used to deliver ablative energy in various forms, e.g., RF, microwave, cryogenic cooling, etc as described herein or known to those of ordinary skill in the art. The device may be held fixedly in the desired location by various methods, e.g., vacuum, magnetically, temporary adhesives, sutures, or any other methods of attaching or approximating the device and tissue.

Figure 8A:
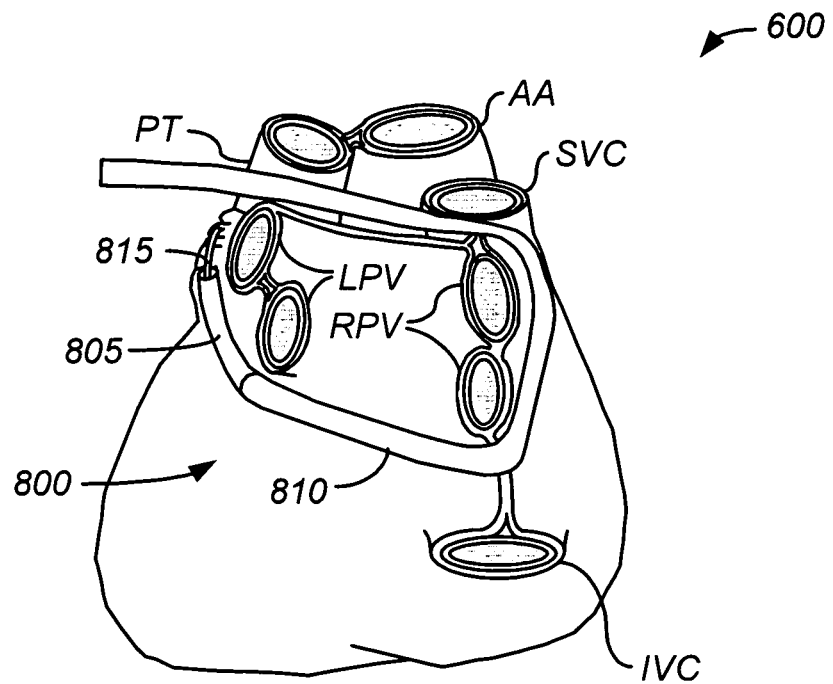
FIGS. 8A to 8D show an example of the endoscopic device advanced about the posterior region of a heart and retracted to deploy a device to facilitate treatment of a supraventricular tachycardia.

FIGS. 8A to 8D show an example of a procedure 600 wherein a steerable endoscopic device is advanced about the posterior region of a heart and then retracted to deploy a device to facilitate treatment of a supraventricular tachycardia. The steerable endoscopic device 800 is capable of reaching regions within the body as described above and as an improvement over laparoscopic procedures. The figures show a posterior view of the heart with the aorta AA and pulmonary trunk PT as anatomical landmarks. FIG. 8A illustrates an endoscopic device 800 having a steerable, controllable distal end 805 and a controllable proximal end 810. In FIG. 8A, at the beginning of the procedure 600 the endoscopic device 800 has been maneuvered into position to initiate deployment of an ablation device 815. It is to be appreciated that in this exemplary procedure 600 the steerable endoscopic device 800 has been maneuvered to the initial deployment point by tracing out a desired deployment or treatment pathway about the pulmonary veins. While illustrated with regard to the pulmonary veins for purposes of the discussion of procedure 600, the utilization of the steerable endoscope is not so limited and may be used to trace out desired treatment pathways about organs, tissues and body portions as desired. FIG. 8A also illustrates the ablation device 815 distal end is attached to the heart using any of the attachment methods described in this application or known to those of ordinary skill in the art.

Figure 8B:
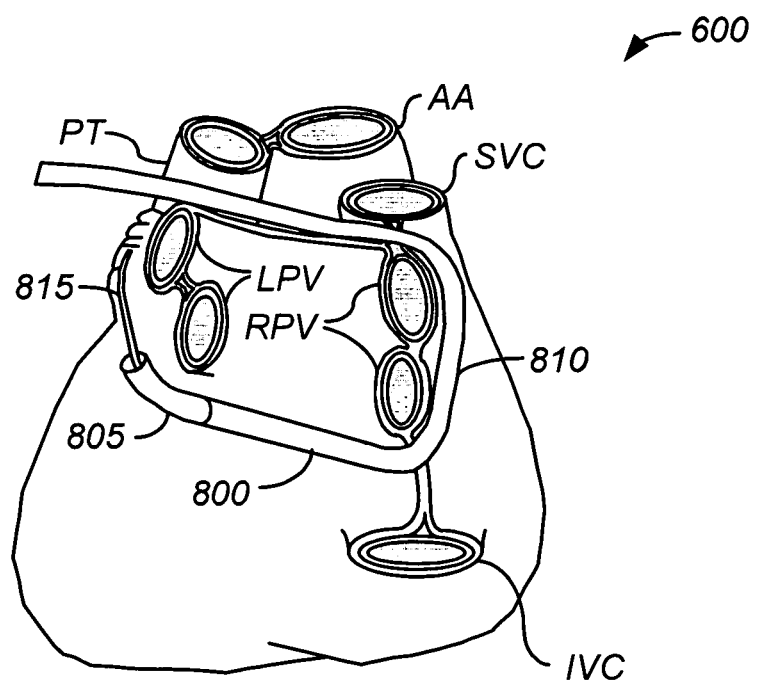
Figure 8C:
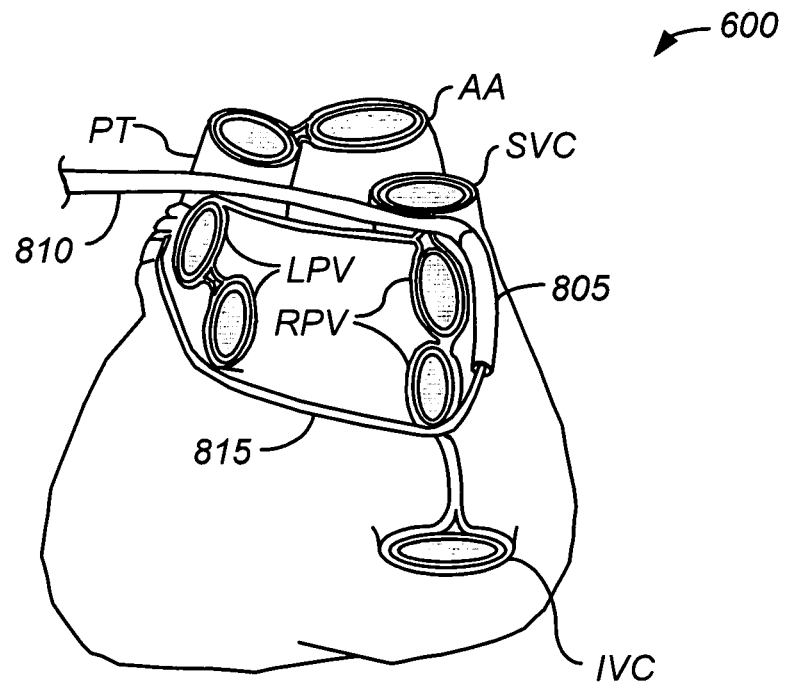
Figure 8D:
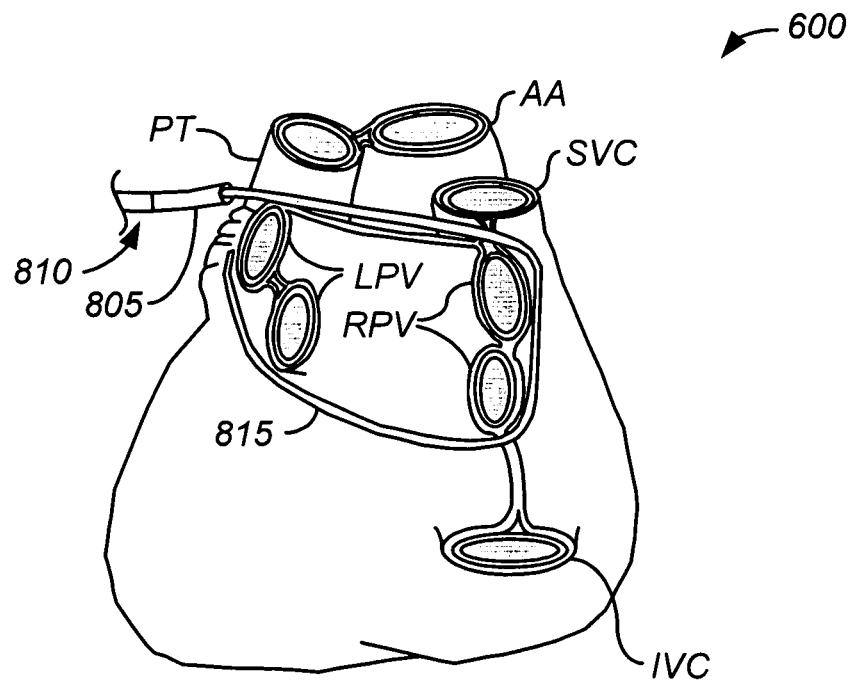

Next, in FIGS. 8B and 8C, the steerable endoscope 800 is withdrawn proximally along the pathway leaving behind the ablation device 815. Finally, in FIG. 8D, the ablation device 815 is completely deployed about the pulmonary veins in the desired deployment pathway created by the steerable endoscope 800. At this point a number of options are available in procedure 600. The endoscope 800 may be withdrawn during the treatment that utilizes the ablation device 815. The endoscope 800 may be utilized to visually inspect the position and orientation of each ablation element distributed along the ablation device 815 in those embodiments where the ablation device 815 comprises a plurality of ablation elements. In this illustrated embodiment, the ablation device 815 has been illustrated as a single ablation element for ease of illustration. The endoscope may also be utilized to ensure the ablation device 815 has been properly deployed into the desired position to facilitate treatment. In addition, the endoscope may be utilized to visually inspect any fasteners or other adhesives or affixing means used to maintain the position of the ablation device 815 relative to the pulmonary veins.

Figure 9:
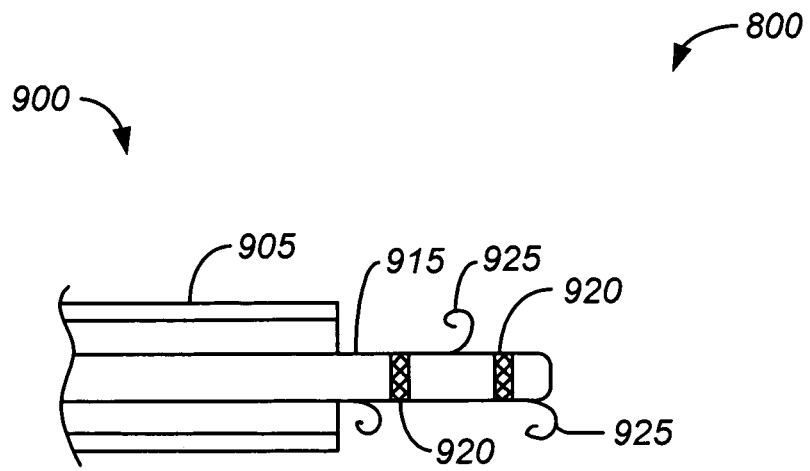
FIG. 9 shows an embodiment of a treatment device having a plurality of fasteners to facilitate contact between the treatment device and the surrounding tissue.

FIG. 9 shows an embodiment of a treatment device having a plurality of fasteners to facilitate contact between the treatment device and the surrounding tissue. An endoscopic device 900 has a controllable, steerable end 905 positioned to deploy or facilitate the deployment of an ablation device 915. The ablation device 915 has a plurality of ablation elements 920. The ablation device 915 also has a plurality of fasteners 925 to increase the contact between the ablation device 915 and the surrounding tissue, organ or body portion to facilitate ablation therapy. Note the position of the fasteners 925 relative to the ablation elements 920 to provide maximum contact between and to ensure the location of the ablation elements 920 relative to the surrounding tissue. The fasteners 925 may be in other positions and may also be of other configurations and type described elsewhere in this application and/or as known to those of ordinary skill in the art.

In another embodiment of the steerable endoscope 900, the fasteners 925 could be configured such that as the steerable tip 905 is withdrawn proximally, the fastener 925 engages the surrounding tissue to secure the position of the ablation device 915. Once the ablation device 915 is positioned, the ablation treatment proceeds as desired. When the ablation treatment is complete, the steerable endoscope 900 is advances proximally from the distal end of the ablation device 915. As the steerable endoscope tip 905 advances distally past a fastener 925, the fastener 925 along with the ablation device 915 are withdrawn into the steerable endoscope 900. It is to be appreciated that any of a wide variety of fasteners may be utilized to engage with the surrounding tissue. For example, the fasteners 925 could be formed from superelastic or shape memory alloy material. The properties of the shape memory alloy material could be selected such that the thermal energy of the body temperature is used to engage the fastener with the surrounding tissue. Alternatively, the shape memory alloy fasteners could be selectively actuated to release the shape memory effect to engage with the surrounding tissue. Engagement with the tissue includes fasteners that do not break the surface of the tissue as well as fasteners that do break the surface of the tissue. While some fasteners may disengage from the surrounding tissue through the movement of the steerable endoscope, it is to be appreciated that a tool or element may be present on or in the distal end of the endoscope 900 to facilitate the disengagement of the fastener from the surrounding tissue.

Figure 10A:
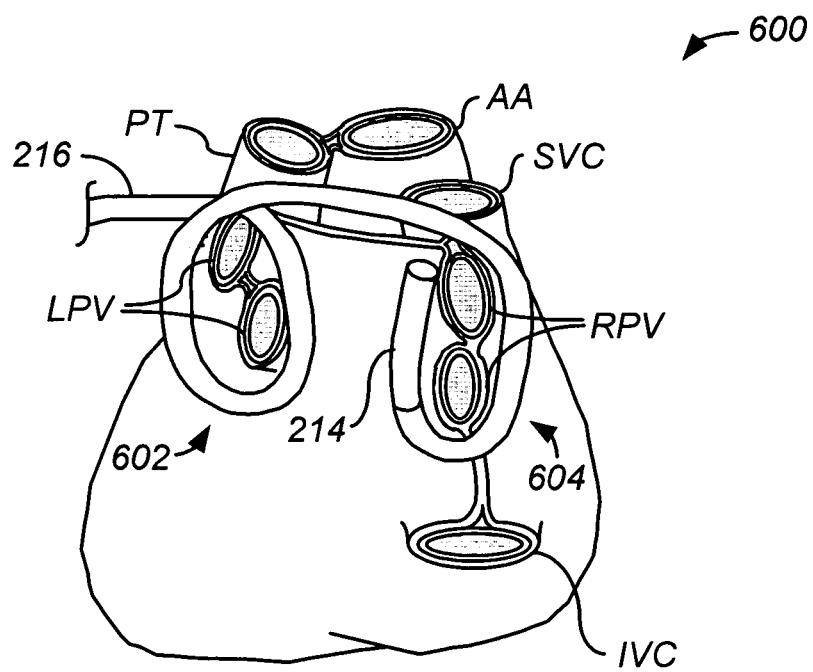
FIGS. 10A and 10B show additional examples of the endoscopic device advanced about the posterior region of a heart to facilitate treatment of a supraventricular tachycardia (FIG. 10A) and a combination of supraventricular and ventricular tachycardia (FIG. 10B).
Figure 10B:
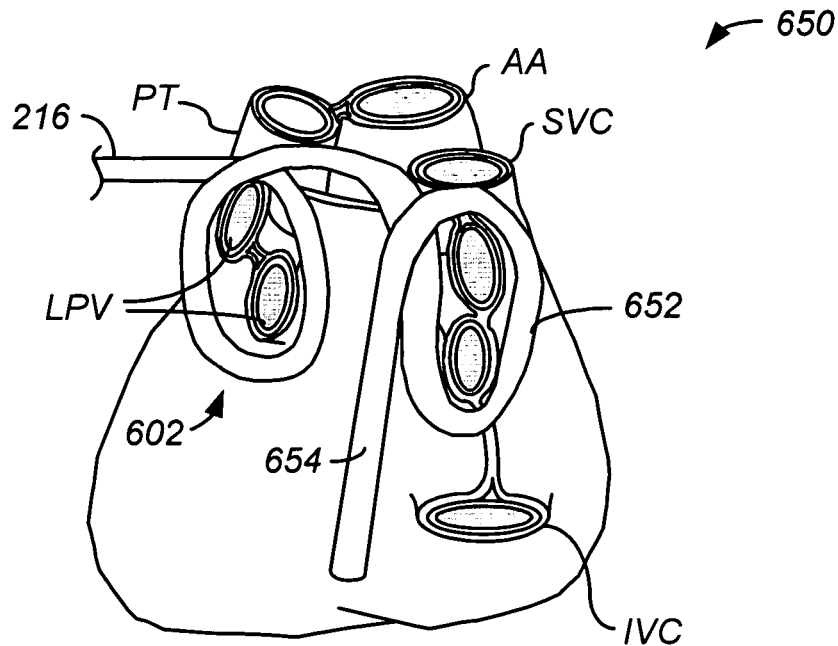

FIGS. 10A and 10B show additional examples of the endoscopic device advanced about the posterior region of a heart to facilitate treatment of a supraventricular tachycardia (FIG. 10A) and a combination of supraventricular and ventricular tachycardia (FIG. 10B). In a specific example, FIG. 10A shows another variation 600 of treating atrial fibrillation where the device may be steered and configured to loop in a continuous manner about the pulmonary vessels in a first encirclement 602 over the left pulmonary vessels LPV and a second encirclement 604 over the right pulmonary vessels RPV. The encircled portions 602, 604 of the endoscope 212 may be activated to ablate the heart tissue only around the pulmonary vessels LPV, RPV or alternatively, it may be activated to ablate the heart tissue along the entire length of both distal portion 214 and proximal portion 216. Moreover, a variety of ablation devices may be delivered to the desired areas, as described above.

In another specific example, FIG. 10B shows another variation 650 of treating atrial fibrillation where the device may be steered and configured to loop in a continuous manner about the pulmonary vessels in a first encirclement 602 over the left pulmonary vessels LPV and a second encirclement 652 over the right pulmonary vessels RPV and then across a portion of the ventricle (654). The encircled portions 602, 652, 654 of the endoscope 212 may be activated to ablate the heart tissue around the pulmonary vessels LPV, RPV and the ventricular portion adjacent 654. Alternatively, it may be activated to ablate the heart tissue along the entire length of both distal portion 214 and proximal portion 216. Moreover, a variety of ablation devices may be delivered to the desired areas, as described above.

Figure 11:
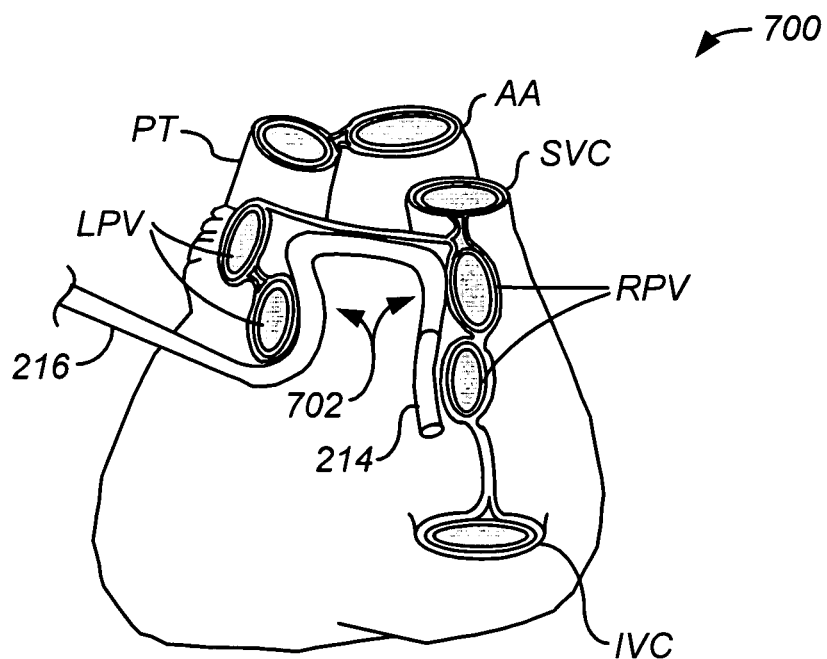
FIG. 11 shows yet another example of a treatment for atrial fibrillation using the endoscopic device.

FIG. 11 shows yet another example of a treatment for atrial fibrillation using the endoscopic device. In a specific embodiment, FIG. 11 shows yet another variation 700 in which the endoscope 216 may be advanced and steered to contact the portions of tissue posteriorly adjacent to the pulmonary vessels LPV, RPV such that an encircled region is formed 702. As illustrated, embodiments of the steerable endoscope of the present invention may be positioned about a portion of the coronary vasculature or other coronary landmarks to facilitate treatments of the heart. In this specific example, the endoscope 216 has been maneuvered using the techniques described herein into a position interior and adjacent the pulmonary veins and extended towards the inferior vena cava. The extreme configurability and controllability of the space and position of steerable endoscopes of the present invention enable placement of therapeutic devices, elements and systems about the heart and elsewhere within the body to facilitate treatment.

Figure 12A:
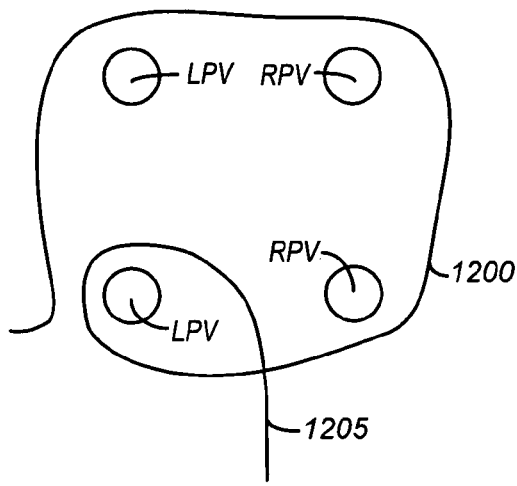
FIGS. 12A and 12D show additional examples of the endoscopic device advanced about the posterior region of a heart to facilitate treatment of a supraventricular tachycardia and/or combinations of supraventricular and ventricular tachycardia.
Figure 12B:
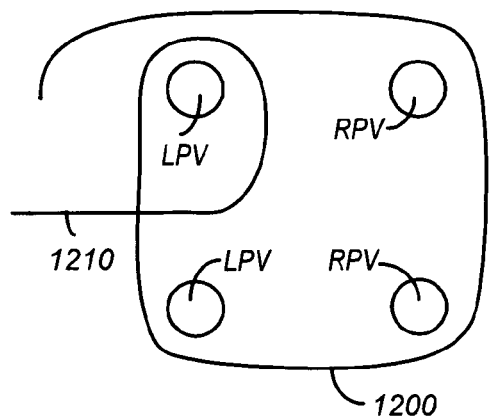
Figure 12C:
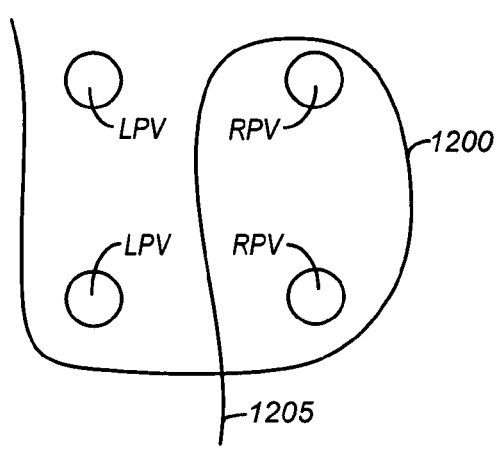
Figure 12D:
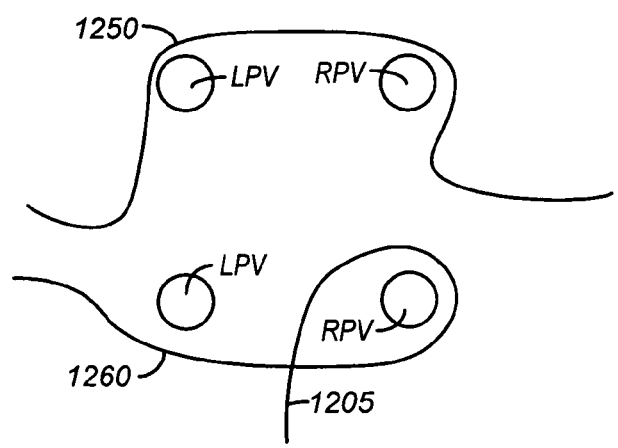

FIGS. 12A and 12D illustrate additional alternative embodiments of steerable endoscopic devices of the present invention advanced about the posterior region of a heart to facilitate treatment of a supraventricular tachycardia and/or combinations of supraventricular and ventricular tachycardia. As described above with regard to FIG. 10A and 10B, the left pulmonary veins (LPV) and right pulmonary veins (RPV) are used as landmarks for purposes of illustration and discussion and not limitation. FIG. 12A illustrates an endoscopic device 1200 positioned about both the LPV and RPV and encircling one of the LPV and then proceeding anteriorly across a ventricular portion of the heart 1205. FIG. 12B illustrates an endoscopic device 1200 positioned about both the LPV and RPV and encircling one of the LPV and then proceeding laterally across a ventricular portion of the heart 1210. FIG. 12C illustrates an endoscopic device 1200 positioned about both the RPV, partially encircling the LPV and then proceeding anteriorly across a ventricular portion of the heart 1205. FIG. 12D illustrates an embodiment of the present invention where two endoscopic devices 1250 and 1260 are utilized to facilitate an ablation therapy. The first steerable endoscopic device 1250 is positioned laterally across the heart and partially encircling a LPV and a RPV. The second endoscopic device 1260 is positioned adjacent a LPV, encircling a RPV and then proceeding anteriorly across a ventricular surface of the heart 1205. It is to be appreciated that the first steerable endoscope 1250 may be used to facilitate a first ablation therapy at the same time, subsequent to or in a sequence with a second ablation therapy facilitated by the second steerable endoscope 1260. As these illustrative embodiments demonstrate, the steerable endoscopes of the present invention may be deployed in a wide variety of circumstances to facilitate an ablation therapy.

Figure 13:
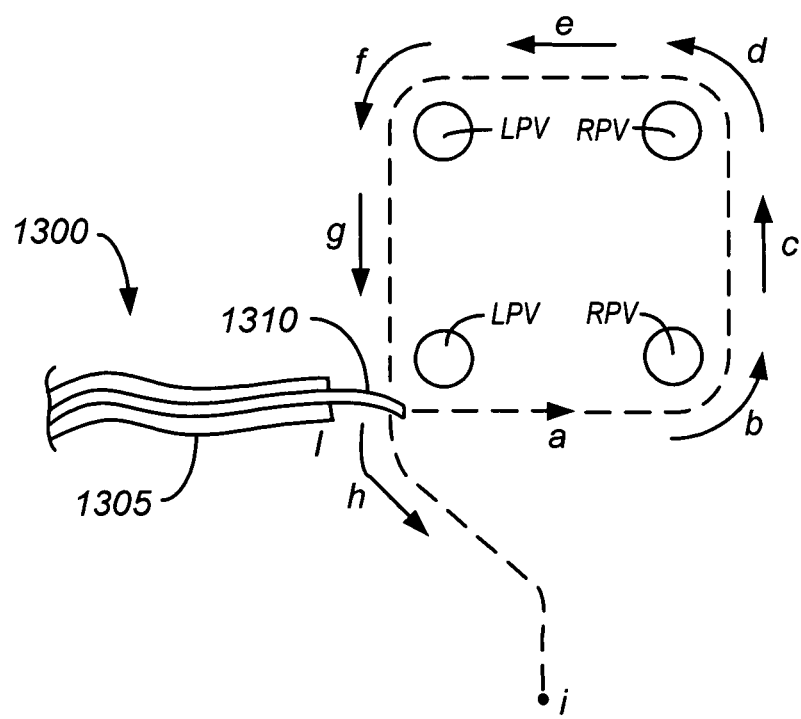
FIG. 13 shows an embodiment of a dual, steerable endoscope of the present invention utilized to facilitate treatment of the heart.

FIG. 13 shows an embodiment of a dual, steerable endoscope 1300 of the present invention utilized to facilitate treatment of the heart. The dual steerable endoscope 1300 includes a first steerable endoscope 1305 and a second steerable endoscope 1310 disposed within the first steerable endoscope 1305. In one embodiment, both endoscopes 1305, 1310 are articulated to an initial condition (I). Thereafter, the second endoscope 1310 proceeds along the pathway (a) through (i) to encircle the LPV, RPV and then proceed across a ventricular portion of the heart. The second endoscope 1310 may proceed along the pathway under control of a user. Alternatively, the second endoscope 1310 may proceed along the pathway by automatically deploying based upon any or a combination of pre-surgical planning imagery, real time imagery, mapping system receiving inputs from a detection or tracking system. In another alternative, the second endoscope 1310 proceeds using a combination of automatic controls and user input.

While described above in an application for treating the heart, it is to be appreciated that the first and second steerable endoscopes may be utilized to access portions of the neurovasculature, and other regions by maintaining the size of the second steerable endoscope to be much less than the size of the first endoscope. For example, the first endoscope may positioned in a first position, affixed in that position to act as a stable platform and/or datum for the second steerable endoscope. From that stable base, the second endoscope may be deployed to facilitate treatments.

Figure 14A:
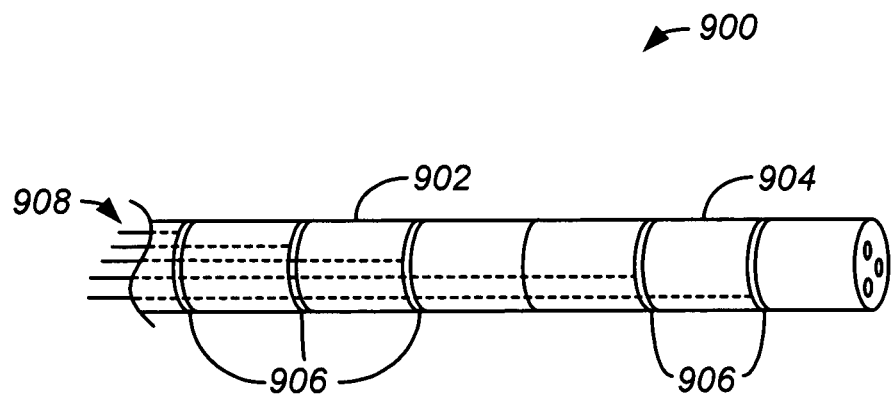
FIGS. 14A to 14C shows side and end views, respectively, of various electrode configurations on the endoscope for tissue ablation treatment.
Figure 14B:
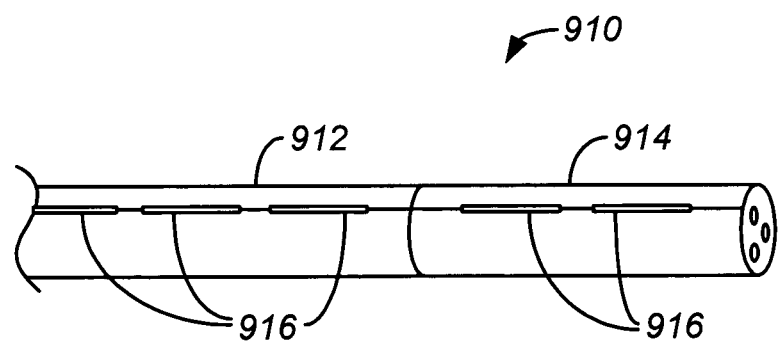
Figure 14C:
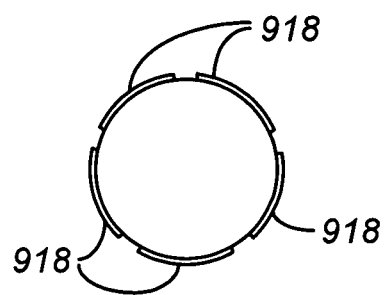

FIGS. 14A to 14C shows side and end views, respectively, of various electrode configurations on the endoscope for tissue ablation treatment. The endoscope 900 may be configured with a number of elements, devices or systems to facilitate treatment. In one specific embodiment, a steerable endoscope of the present invention may have a plurality of electrodes disposed along its outer surface to facilitate the tissue ablation along the length, or selected regions of length, of the endoscope, as shown as described herein. The figure shows the steerable distal portion 904 and part of the automatically controllable proximal portion 902 as one example of electrode placement over the endoscope 900. As seen, one or any number of electrodes 906 may be circumferentially positioned, e.g., ring-shaped, along the length of endoscope 900 at intervals. The electrodes 906 are shown positioned at uniform intervals in this variation; however, they may be configured in any random, arbitrary, or specified locations over the outer surface of the endoscope 900. Each of the electrodes 906 may be electrically connected via corresponding wires 908 to a power supply and/or controller. Thus, all the electrodes 906 may be configured to operate simultaneously or to operate only selected electrodes 906 which may be in contact with tissue. In yet another variation, various ablation devices may be delivered to the desired areas, again as described above.

FIG. 14B shows another variation in endoscope 910 in which electrodes 916 may be configured to extend longitudinally over the proximal portion 912 and/or distal portion 914. The electrodes may be configured to extend in a continuous strip along the endoscope length or the electrodes 916 may be alternatively configured to extend in a segmented manner longitudinally over the endoscope 910, as shown. Having segmented electrodes 916 may allow for selected electrodes to be activated during tissue ablation. Although FIG. 14B shows a single line of electrodes 916 for illustration purposes, multiple lines of electrodes may be positioned over the outer surface of the device, as shown in the example of FIG. 14C, which illustrates multiple lines of electrodes 918 spaced uniformly around the circumference of the endoscope surface.

These examples described above are intended to be illustrative and are not intended to be limiting. Any number of other configurations may be accomplished with the endoscopic device due to the ability of the device to steer and configure itself such that excessive contact with surrounding tissue is avoided. Moreover, access to any number of various regions within the thoracic cavity with minimal or no damage to surrounding tissue and organs may be accomplished using the controllable endoscopic device above. Other examples for treatment using the endoscope may include, but not limited to, lead placement, implantable device placement, treatment on the lungs such as emphysema treatments, etc.

Depending upon the treatment being facilitated, it may be advantageous to increase the degree of contact or ensure the position between the treatment tool, element, or device and the tissue, organ or portion of the body receiving the treatment. Examples of means for increasing contact or affixing the position of a treatment device include: biocompatible adhesives, glues and gels either alone or in combination with staples, suction, wires, barbed and barb-less hooks or hook shaped to loop around specific anatomy. One example of a hook shaped to loop around specific anatomy includes J-shaped hooks to loop, at least partially, about the coronary vasculature. For example, a J-shaped hook may be shaped and configured to at least partially encircle a pulmonary vein. In another example, wires, staples or other fastening components may be formed from shape memory alloy material such as, nitinol or other suitable, biocompatible shape memory alloy material. The shape memory alloy fastener could be held in a first or stowed condition while navigating to the site prior to facilitating treatment. Once the treatment device is positioned, the shape memory alloy fastener could be activated and use the shape memory effect to affix the treatment device into the desired position.

In another embodiment, a steerable endoscope having a magnetic portion could be deployed about the tissue, organ or region of the body to facilitate treatment. Thereafter, the steerable endoscope could be used as a guide for the placement of an ablation system. Permanent magnets or electromagnets could be used to magnetically couple the ablation system in a desired position adjacent the steerable endoscope. Once the treatment was completed, the magnetic field is broken and the ablation system and steerable endoscope withdrawn could be deployed in proximity-to the steerable endoscope and a In another embodiment, the steerable endoscope itself may be looped around the organ, tissue or portion of the body to undergo treatment and then secured to itself in order to facilitate treatment. Alternatively, the distal end of the endoscope could be anchored with a dissolvable suture or other dissolvable biodegradable fastener that remains in place after the ablation treatment is completed and is then absorbed into the tissue or dissolves.

In addition, an array of needles may be configured along the length or a portion of the length of the ablation device or steerable endoscope or both. In one embodiment, an array of conductive needles are arranged to improve contact between an RF ablation based delivery system and the tissue undergoing treatment. In addition to needle arrays, other suitable elements may be employed to improve the effectiveness of other ablation modalities. It is to be appreciated therefore that while needle arrays are described as increasing the effectiveness of the delivery of RF ablation energy, other elements and configurations may be used to increase the effectiveness of other ablation therapy modalities. Alternatively, for non-energy based ablation, such as ablation techniques that use lacerations of the tissue, then the elements could be any suitable device for cutting or otherwise altering the tissue to achieve a therapeutic affect.

FIGS. 15A and 15B show an embodiment of a needle array in a retracted (FIG. 15A) and a deployed (FIG. 15B) configuration. A portion of a steerable endoscope or ablation element 1500 is shown in cross section. Ablation needles 1505, 1510 are attached to backing plate 1515. The needles are maintained in the stowed configuration (FIG. 15A) with the backing plate retracted to reduce the risk of inadvertent tissue damage as the steerable endoscope or ablation system is advanced to the treatment site. In the stowed configuration, the needles 1505, 1510 remain below the steerable endoscope or ablation element exterior surface 1502. Once in position, the backing plate 1515 is advanced to the deployed condition (FIG. 15B). In the deployed position, the needles 1505, 1510 protrude beyond the steerable endoscope or ablation element exterior surface 1502. When positioned in the body for treatment, the needles 1505, 1510 would make suitable contact with the surrounding tissue, organ or body portion to facilitate treatment.

It is to be appreciated that the backing plate may be moved between the retracted and deployed configuration utilizing any of a number of techniques. Examples of such techniques and methods include, mechanical drives, hydraulics, motors, actuators, permanent magnets, electromagnets, spring loaded actuators, vacuum, or other conventional actuation means. Alternatively, the actuation means could be any suitable actuation force capable of displacing the backing plate 1515 to urge a portion or all of a needle array from a retracted position into a deployed position and hence into suitable contact with the organ, tissue or body portion to receive treatment.

In an alternative embodiment, the backing plate 1515 could be continuously biased outwardly, here, outwardly indicates a position where the needles would move into a deployed configuration. The ablation element or steerable endoscope having the needle array could be covered with a moveable sheath. Once the ablation element or moveable endoscope is in the desired position, the sheath is retracted releasing the backing plate bias and allowing the needles to move into a deployed configuration.

The illustrated embodiment illustrates a pair of needles in cross section. There may be additional needles arranged adjacent and similarly disposed as the needles 1505, 1510. The additional needles may be, for example, arrayed in a regular continuous pattern as in FIG. 16. Alternatively, a single needle or array on continuous, discontinuous or random arrangement of needles may be used. In other configurations, more than teo needles may be used. The illustrated needles 1505, 1510 have a separation angle $\theta_1$ The separation angle may vary from 0 to 180 degrees in one embodiment, from 0 to 70 degrees in another embodiment or from 0-30 degrees in yet another embodiment depending upon application. In multiple needle applications (i.e., needle arrays having two or more separation angles), the needles may have a regular separation angle meaning that the needles are at regular angular intervals. Alternatively, the needles in a multiple needle configuration may be placed in non-regular or variable separation angles.

In addition to the angular placement of the needles in a needle array, the spacing between needles may also be continuous or variable. The needles may be arranged into a single continuous segment with uniform spacing. Such a uniform array of needles is illustrated in FIG. 16. The ablation element or steerable endoscope section configured for ablation 1600 is shown in FIG. 16. Needles 1610 are shown in a single segment or grouping of needles 1605.

FIG. 17 shows an embodiment of a needle array segment 1700 having three sections (1705, 1710 and 1715) showing a variety of needle spacing configurations. The needle array segment 1700 illustrates how a nearly limitless variety of spacing configurations may be combined to obtain a desired needle array configuration to facilitate an ablation treatment. Section 1705 includes an upper array of needles 1726, 1728 and 1730 aligned in a continuous uniform fashion above a lower array of needles 1720, 1722 and 1724. This configuration is similar to section 1600 in FIG. 16. Like section 1705, the upper array of section 1710 has evenly spaced needles 1732, 1734 and 1736. The lower array of needles have only one needle aligned to the upper array. Needle 1738 is aligned with needle 1732. There is no needle in the lower array that corresponds to needle 1736. A plurality of needles (1740, 1741 and 1742) are spaced across from upper array needle 1734. The section 1710 illustrates how there may be needle to needle correspondence (1732, 1738), no correspondence (1736) or one to many correspondence (1134, 1740, 1741, 1742) between the needles in the upper and lower arrays of a section.

Section 1715 further illustrates the configurabilty of the needle arrangements. Both the upper needles 1750, 1752, 1754 1756 and lower needles 1766, 1768, 1770, 1771, 1772, 1773 illustrate variable spacing. In addition, there is no alignment between the upper and lower arrays. In addition, section 1715 illustrates a middle array having upper needles 1758, 1760 spaced apart from lower needles 1762, 1764. In the illustrated embodiment, the upper and lower needles are aligned but that need not be the case in all embodiments. Additionally, the middle array is illustrated without alignment to the upper array and the lower array. This need not be the case in all embodiments. In some embodiments, the middle array may be aligned with all or part of either a lower or an upper array. Accordingly, a needle pattern within a section could be predetermined and selected to facilitate a desired ablation treatment. Moreover, using pre-surgical planning techniques, the type, number, amount and ablation pattern could be predetermined and an appropriate combination of segments, sections and needles arrays could be loaded into a steerable endoscope or otherwise delivered utilizing a steerable endoscope to facilitate treatment.

Figure 18A:
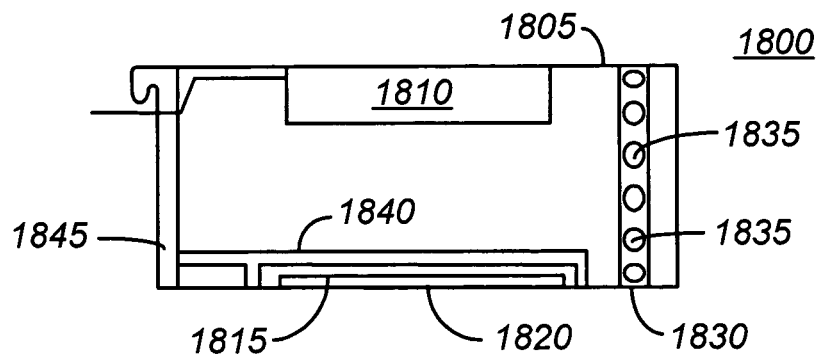
FIG. 18A and 18B show a side and isometric view of an embodiment of a treatment device of the present invention.
Figure 18B:
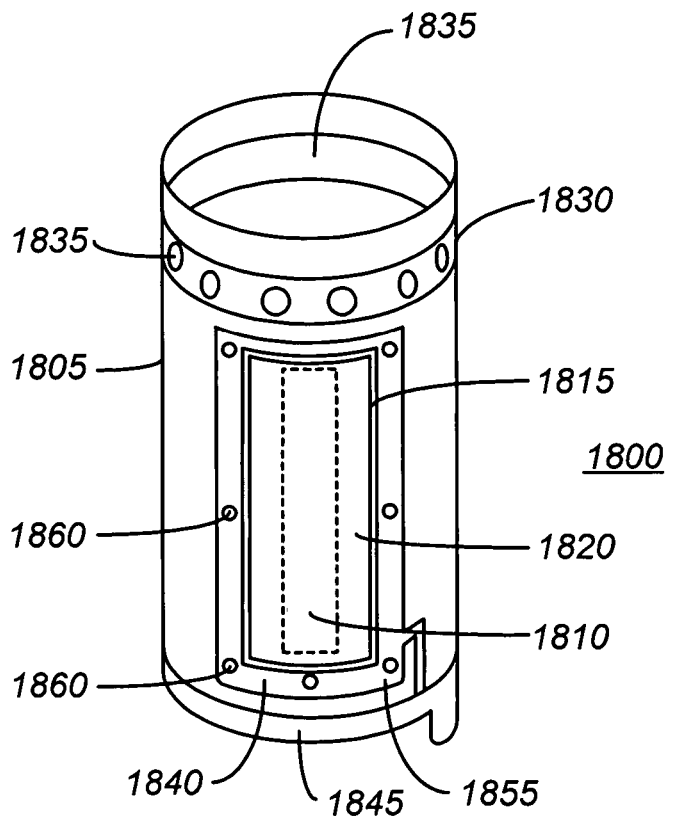

FIGS. 18A and 18B show a side and isometric view of an embodiment of a tunable treatment device of the present invention. The tunable treatment device 1800 includes an ablation element 1810 within a housing 1805. The housing 1805 also includes an opening 1815 that allows the energy generated by the ablation element 1810 to pass outside of the housing. The opening 1815 is fitted with a cover 1820 that forms a seal between the environment the tunable treatment device 1800 is positioned in and the interior of the housing 1805. In one embodiment, the housing 1805 is made of a first material and the cover 1820 is made of a second material. With respect to the energy generated or provided by the ablation element 1810, the first material transmits less of the energy generated by the ablation element 1810 than the second material. In another embodiment, the first material acts as a shield separating the ablation energy generated by the ablation element and the surrounding environment. The second material acts as a transmission window or opening in an otherwise shielded housing. The transmission window or opening thus allows energy provided by the ablation element to be selectively passed via the opening into the tissue, organ or environment positioned adjacent the cover 1820. Thus, the advantageous combination of shielding and openings allow for more precise delivery of the ablation energy to the desired tissue, organ or location while shielding the surrounding area from the ablation energy.

The tunable ablation delivery device 1800 is also provided with a detector 1830 for detecting a physiological indication useful in administering the ablation therapy. The detector 1830 may comprise a plurality of detection elements arrayed about the housing 1805. In the illustrated embodiment, the detector 1830 includes a plurality of detection elements 1835. The detection elements 1835 are arranged at regular intervals about the perimeter of the housing 1805. A reading may be obtained from each element and then analyzed to determine which element or elements obtained the best reading for the physiological parameter being measured. Once that determination is made, the tunable ablation device 1800 may then be oriented to place the opening 1815 into position to facilitate ablation treatment.

Figure 19:
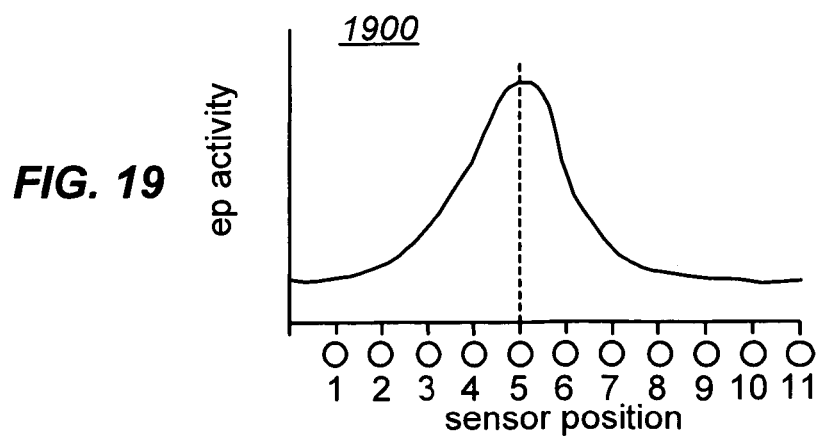
FIG. 19 shows a graph illustrating a technique to optimize placement of a device to facilitate therapy.

In one specific example, the tunable ablation delivery device 1800 may be modified to facilitate an ablation treatment on the pericardium of the heart. In this example, the detection elements 1835 may be elements capable of detecting electrophysiological (EP) activity. For example, the detection elements 1835 could detect electrophysiological (EP) activity by detecting ECG activity. An example of the readings and/or signal strength obtained by each detector 1835 is illustrated in FIG. 19. FIG. 19 shows a graph illustrating a technique to optimize placement of a tunable ablation device to facilitate therapy. Using conventional software, hardware and optimization techniques, the detection elements 1835 may be used to localize the position, relative to the housing 1805, where the desired amount of physiological indication occurs. In the graph 1900 the desired activity is the peak EP activity. According to the graph 1900, the peak EP activity occurs in proximity to sensor position 5. This information can then be used by the control system that articulates, rotates, translates or otherwise positions the tunable ablation element 1800 to position the tunable ablation element 1800 into a position that facilitates an ablation treatment in the vicinity of sensor 5. In the specific embodiment illustrated in FIGS. 18A and 18B, the tunable ablation device 1800 would be rotated under the control of a control system having the relative position and orientation of the plurality of elements 1835 and the opening 1815 and ablation element 1810. The tunable ablation device 1800 would be rotated under the control of a control system using for example, the engagement element 1845, to align the opening 1815 and/or cover 1820 into the orientation of sensor 5.

Figure 18C:
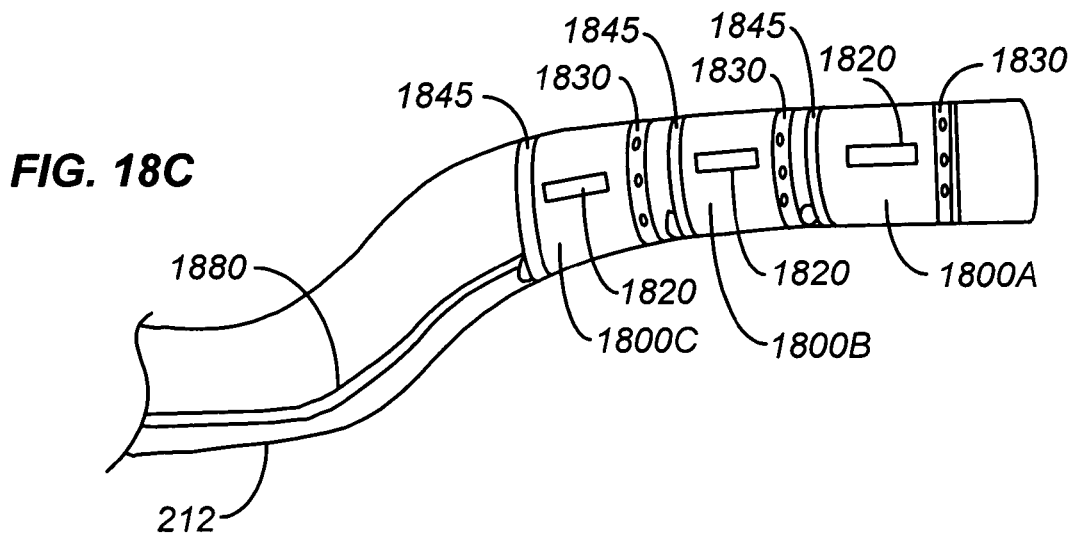
FIGS. 18C and 18D show a plurality of the treatment devices in optimized positions for facilitating a therapy.
Figure 18D:
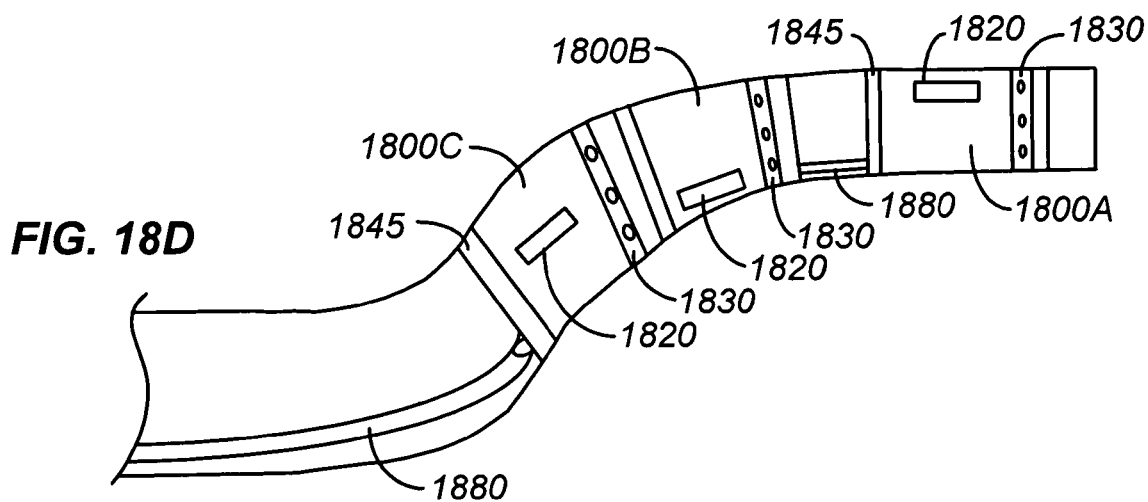

An example of how a plurality of tunable ablation elements may be advantageously deployed to increase the effectiveness of an ablation therapy will now be described with reference to FIGS. 18C and 18D. Three tunable ablation elements 1800A, 1800B and 1800C are positioned within a steerable endoscope 212 of the present invention. In FIG. 18C the three ablation elements have reached the deployment point for ablation element 1800A. Note that in the initial position before optimizing any of the tunable ablation elements 1800A, B or C, the windows 1820 are aligned. As described above the detectors 1830 on ablation element 1800A are used to improve the effectiveness of the ablation element within the tunable ablation element 1800A by indicating a desired position for applying the ablation therapy. As shown in FIG. 18B, the determined position of the element 1800A is when the window 1820 rotated into a slightly upward position from the initial position. Additionally, the mechanical linkage 1845 has been disengaged so that the control cable/component 1880 no longer rotates the element 1800A. In addition, the fixation elements for element 1800A have been omitted for clarity but have engaged to fix the position of element 1800A. FIG. 18D also illustrates how the controller cable/component 1880 has utilized the detector 1830 onboard element 1800B to optimize the position of the window 1820. Note that the window 1820 for element 1800B is rotated downward. At this point, the fixation elements for element 1800B are engaged to fix the position of the element 1800B. Thereafter, the linkage 1845 for element 1800B is released so that element 1800C may be positioned and then optimized as described herein for elements 1800A and 1800B. Accordingly, there are configurations of the tunable ablation elements where the windows of adjacent ablation elements are not in alignment but rather reflect an alignment of localized optimization for that ablation element.

In an alternative embodiment, the detector for detecting a physiological indication could also be a single detector. The single detector could be actuated to move about the surface of the tunable ablation delivery device 1800 measuring the indication. The obtained measurements could then be used to assist in positioning the ablation element 1810 and opening 1815 to facilitate treatment. In one specific embodiment, the single detector could move about the perimeter of the tunable ablation device and provide strength of indication relative to position information similar to FIG. 19.

A securing member 1840 is also provided to hold the tunable ablation device 1800 in the desired position during the readings from the indicator elements 1835, or after rotation of the ablation device into the desired position for facilitating treatment. In the illustrated embodiment, the securing member 1840 may be a vacuum manifold 1855 having a plurality of suction ports 1860. In a preferred embodiment, the securing means is releasable from the surrounding tissue, organ or region of interest to facilitate movement to align the ablation element for treatment or for easy removal once the treatment is complete.

Figure 20:
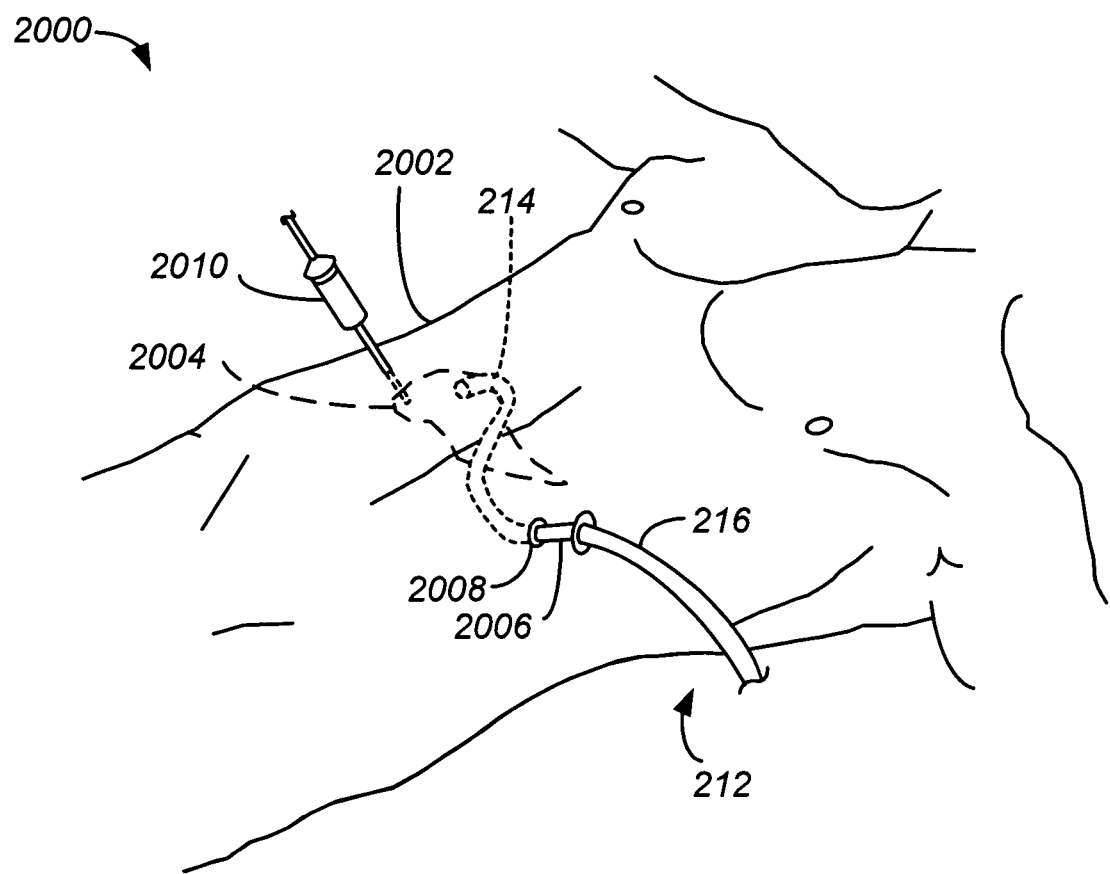
FIG. 20 shows an example of a procedure within the peritoneal cavity which may be performed with the endoscopic device.

The endoscope device may also be utilized for procedures within the peritoneal cavity. Potential applications may include minimally invasive surgery for urologic, bariatric, and liver surgery. Moreover, minimally invasive access may be achieved for treatments in spinal or orthopedic surgery as well. FIG. 20 shows an example of a procedure 2000 within the peritoneal cavity which may be performed with the endoscopic device. FIG. 20 shows an example of a procedure 2000 within the peritoneal cavity using the endoscopic device 212. The endoscope 212 may be introduced into patient 2002 through an incision 2008 via a port, which may also function as a datum 2006, as described above. The distal portion 214 may be steered to avoid various organs while being 2004. The distal portion 214 of the endoscope 212 may accordingly be steered while the proximal portion 216 may be automatically controlled to follow a path defined by the distal portion 214 which minimizes contact with the surrounding and adjacent tissue and organs. One or more laparoscopes 2010 may optionally be used in combination with the endoscope 212 to assist with the surgical procedure. Once the distal portion 214 is posteriorly positioned of the liver 2004, various tools or treatment devices may be advanced through the endoscope 212 from the proximal end to effect the desired treatment. Although this example shows treatment of the liver 2004 using the endoscope 212, this is intended to be illustrative of other organs or procedures that may be effectively treated utilizing embodiments of the endoscope 212.

As the above discussion illustrates, steerable endoscopic systems of the present invention may advantageously utilized to facilitate a wide variety of procedures. When utilized to facilitate an ablation therapy, the ablation element, device or system may be part of the segmented steerable endoscope, deployed within a working channel or other passage created by the steerable endoscope, or a combination of fixed and moveable treatment elements, device or systems. Accordingly, steerable endoscopes of the present invention may, in one embodiment, facilitate treatment by deploying an ablation element, device or system affixed to the endoscope to a treatment location in a treatment position. The endoscope remains in place during the treatment and, when complete, retracts from the treatment position.

In another variation, the steerable endoscope is utilized to deploy and/or inspect the placement of a treatment device, is then withdrawn while the treatment proceeds. Thereafter, the steerable endoscope retrieves the treatment device. In yet another variation, the steerable endoscope may be inserted into a treatment area into a desired treatment pathway. Next, the steerable endoscope is retracted to leave the treatment device in place along the desired treatment pathway. The steerable endoscope may remain in place for visualization of the treatment as it proceeds, monitor a physiological indication or otherwise support the treatment. Alternatively, the steerable endoscope may withdraw from the treatment area or completely from the body. After the treatment is complete, the steerable endoscope may be advanced along the treatment device to remove/store the treatment device as the endoscope proceeds distally along the treatment device. Once the treatment device has been collected into the endoscope, the endoscope is withdrawn. Accordingly, there have been shown various ways to position a treatment element, device or system within a body, affix or otherwise maintain the position of the treatment device relative to the area or areas of treatment to increase the effectiveness of the treatment or therapy being performed.

Separately or in combination with the techniques described above, various imaging and control systems may be used to facilitate control of the steerable endoscope. For example, the steerable endoscope may proceed along and envelope a deployed treatment device utilizing a recorded pathway to retrace steps used to place the treatment device. The steerable endoscope may also track a way point set to indicate the next fastener where the fastener is in a preprogrammed position, in an position identifiable using an imaging system or the fastener is other wise configured for easy identification, such as through use of an RFID, for example. The steerable endoscope may also use an imaging system for guidance in recovering a treatment device. The steerable endoscope may also utilize fly by wire techniques to fly by wire using the treatment device as the wire. In yet another embodiment, the treatment device could be automatically withdrawn into the steerable endoscope using mapping, imaging or other system controls to retrace track or otherwise dislodge or disengage the treatment device from the internal position to perform a treatment.

Embodiments of the present invention may also include tools, devices or systems to pierce, lacerate, cut, puncture, or otherwise provide a passage or controlled perforation of tissue to allow access of the steerable, guided endoscope into the region of interest. In a neurological application for accessing the brain, such as device would be suited for creating a suitable opening in the dura for example. In a cardiovascular application for accessing the heart, such as device would be suited for creating a suitable opening in the pericardium for example. The tools, devices or systems to pierce, lacerate, cut, puncture, or otherwise provide a passage or controlled perforation to enable passage of the endoscope may be disposed permanently on the distal end of the scope. Alternatively, the tools, devices or systems may be mounted on the distal end of the endoscope but be positionable between a retracted and extended position to help minimize the risk of inadvertent damage while the endoscope is moving within the body to the region of interest. In another alternative, the tools, devices or systems may be provided conventionally via a working channel in the endoscope. Examples of the tools, devices or systems include scissors, electrocaulitry devices and systems, small snips, shaped blades and shaped tips.

While embodiments of the present invention have been shown and described as dispensing treatment within the brain, cranial interior, the interior of the heart, the exterior of the heart, it is to be appreciated that embodiments of the methods and apparatus of the present invention may be used in other applications as well. For example, embodiments of the invention may be used to facilitate treatment of disorders of other organs and portions of the body, for example, the stomach, the gastrointestinal tract, the esophagus, the bladder, the liver, the kidneys and the lungs. Additionally, embodiments of the present invention may be used to facilitate treatment of localized disorders within the body, portions of the body or a disorder of a physiological system.

The applications of the devices and methods discussed above are not limited to regions of the body but may include any number of further treatment applications. Other treatment sites may include other areas or regions of the body. Additionally, the present invention may be used in other industrial and commercial environments such as exploratory procedures on piping systems, ducts, internal inspection of mechanical systems including automotive, aeronautical, aerospace, and marine systems and equipment, etc. Modification of the above-described assemblies and methods for carrying out the invention, and variations of aspects of the invention that are obvious to those of skill in the art are intended to t within the scope of the claims.

We claim:

1. A system for performing a treatment of a condition related to an electrophysiological indication within a peritoneal cavity or a thoracic cavity of a body, comprising: a system for detecting electrophysiological activity within the peritoneal cavity or thoracic cavity and localizing a position of a relative peak of the detected electrophysiological activity; a system for providing imaging of a portion of the body related to the electrophysiological indication within the peritoneal cavity or the thoracic cavity; and a steerable medical device comprising a segmented endoscope having a steerable distal end and a controllable proximal end, the proximal end comprising a plurality of segments individually and automatically under the control of a computer controller that is in communication with, and configured to receive information from, the system for detecting and localizing and the system for providing imaging, wherein in response to the received information the computer controller automatically controls the controllable proximal end within the peritoneal cavity or the thoracic cavity to minimize contact between the plurality of segments and tissue unrelated to the electrophysiological indication within the peritoneal cavity or the thoracic cavity.

2. The system according to claim 1 further comprising a signal indicating the position of the medical device relative to the peak electrophysiological activity.

3. The system according to claim 1 wherein the medical device has a position within the body that is automatically controlled to facilitate a treatment of a condition related to the electrophysiological indication within the body.

4. The system according to claim 1 wherein the electrophysiological indication represents a disorder of an organ.

5. The system according to claim 4 wherein the organ is the liver.

6. The system according to claim 4 wherein the organ is the kidney.

7. The system according to claim 1 wherein the indication is in tissue.

8. The system according to claim 1 wherein the electrophysiological indication is related to a disorder or disease of the heart.

9. The system according to claim 1 wherein the electrophysiological indication is related to a urological disorder or disease.

10. The system according to claim 1 wherein the electrophysiological indication is related to a bariatric disorder or disease.

11. A medical system comprising:
a system that detects electrophysiological activity within a patient's body and localizes a position of a relative peak of the detected electrophysiological activity, wherein the peak indicates a condition to be treated;
a system that images a portion of the body related to the condition;
a flexible medical device comprising a steerable distal end portion and a proximal end portion; and
a computer controller, wherein the computer controller receives inputs from the system that detects and localizes and from the system that images, and wherein, in response to a detected position of the medical device received by the computer controller, the computer controller automatically controls segments of the proximal end portion of the flexible medical device to minimize traumatic contact between the controlled segments and tissue unrelated to the condition as the flexible medical device is advanced or withdrawn.

12. The system of claim 11 further comprising:
a transducer that generates a signal that indicates a position of the flexible device-relative to a location of the electrophysiological indication.

13. The system of claim 11 further comprising:
a controller feature that automatically positions the flexible device to facilitate treatment of the condition.

14. The system of claim 11:
wherein the electrophysiological indication is located on a dorsal portion of the heart; and
wherein the tissue unrelated to the condition comprises tissue in the thoracic cavity.

* * * * *